(12) United States Patent
Rosen et al.

(10) Patent No.: US 9,999,490 B2
(45) Date of Patent: Jun. 19, 2018

(54) INTRA-VAGINAL DEVICES AND METHODS FOR TREATING FECAL INCONTINENCE

(71) Applicant: Pelvalon, Inc., Sunnyvale, CA (US)

(72) Inventors: Miles Harris Rosen, Palo Alto, CA (US); Steven Lawrence Herbowy, Palo Alto, CA (US); Jared Goor, Sunnyvale, CA (US); Narvel M. Brooks, Sunnyvale, CA (US)

(73) Assignee: Pelvalon, Inc., Sunnyvale, CA (US)

( * ) Notice: Subject to any disclaimer, the term of this patent is extended or adjusted under 35 U.S.C. 154(b) by 798 days.

(21) Appl. No.: 14/181,569

(22) Filed: Feb. 14, 2014

(65) Prior Publication Data
US 2014/0275743 A1 Sep. 18, 2014

Related U.S. Application Data

(60) Provisional application No. 61/764,960, filed on Feb. 14, 2013.

(51) Int. Cl.
*A61F 2/00* (2006.01)

(52) U.S. Cl.
CPC ............ *A61F 2/0031* (2013.01); *A61F 2/005* (2013.01); *A61F 2/0027* (2013.01); *A61F 2250/0007* (2013.01)

(58) Field of Classification Search
CPC .... A61F 2/0004; A61F 2/0009; A61F 2/0013; A61F 2/0018; A61F 2/0022; A61F 2/0027; A61F 2/0031; A61F 2/0036; A61F 2/004; A61F 2/005; A61F 2/93
USPC .............. 600/29, 31; 128/834, 836
See application file for complete search history.

(56) References Cited

U.S. PATENT DOCUMENTS

| | | | |
|---|---|---|---|
| 186,469 | A | 1/1877 | Fowler |
| 1,282,881 | A | 10/1918 | Landis |
| 2,475,071 | A | 7/1949 | Thomas |
| 2,638,093 | A | 12/1952 | George |
| 3,554,184 | A | 1/1971 | Habib |
| 3,646,929 | A | 3/1972 | Bonnar |
| 3,675,656 | A | 7/1972 | Hakim |
| 3,705,575 | A | 12/1972 | Edwards |
| 3,709,215 | A | 1/1973 | Richmond |
| 3,797,478 | A | 3/1974 | Walsh et al. |
| 3,831,583 | A | 8/1974 | Edmunds, Jr. et al. |
| 3,841,304 | A | 10/1974 | Jones |
| 3,866,611 | A | 2/1975 | Baumrucker |
| 3,882,852 | A | 5/1975 | Sinnreich |
| 3,903,894 | A | 9/1975 | Rosen et al. |
| 4,019,499 | A | 4/1977 | Fitzgerald |
| 4,031,886 | A | 6/1977 | Morhenn |

(Continued)

FOREIGN PATENT DOCUMENTS

| | | |
|---|---|---|
| DE | 2438691 | 8/1974 |
| EP | 0068318 | 1/1983 |

(Continued)

OTHER PUBLICATIONS

International Search Report and Written Opinion, PCT/US2014/0016549, dated Jun. 24, 2014, 17 pages.

(Continued)

*Primary Examiner* — Catherine B Kuhlman
(74) *Attorney, Agent, or Firm* — Fish & Richardson P.C.

(57) ABSTRACT

Disclosed herein are devices and methods for intra-vaginal bowel control.

31 Claims, 29 Drawing Sheets

(56) References Cited

U.S. PATENT DOCUMENTS

| | | |
|---|---|---|
| 4,307,716 A | 12/1981 | Davis |
| 4,428,365 A | 1/1984 | Hakky |
| 4,587,954 A | 5/1986 | Haber |
| 4,669,478 A | 6/1987 | Robertson |
| 4,686,985 A | 8/1987 | Lottick |
| 4,786,276 A | 11/1988 | Haber |
| 4,823,814 A | 4/1989 | Drogendjik et al. |
| 4,846,818 A | 7/1989 | Keldahl et al. |
| 4,854,990 A | 8/1989 | David |
| 4,946,449 A | 8/1990 | Davis, Jr. |
| 4,981,470 A | 1/1991 | Bombeck, IV |
| 5,007,894 A | 4/1991 | Enhoming |
| 5,041,077 A | 8/1991 | Kulick |
| 5,147,301 A | 9/1992 | Ruvio |
| 5,224,494 A | 7/1993 | Enhoming |
| 5,306,226 A | 4/1994 | Salama |
| 5,370,690 A | 12/1994 | Barrett |
| 5,474,518 A | 12/1995 | Velazquez |
| 5,520,606 A | 5/1996 | Schoolman et al. |
| 5,545,176 A | 8/1996 | Murtfeldt |
| 5,593,443 A | 1/1997 | Carter et al. |
| 5,603,685 A | 2/1997 | Tutrone, Jr. |
| 5,611,768 A | 3/1997 | Tutrone, Jr. |
| 5,702,421 A | 12/1997 | Schneidt et al. |
| 5,733,230 A | 3/1998 | Sawchuck et al. |
| 5,782,745 A | 7/1998 | Benderev |
| 5,884,629 A | 3/1999 | O'Brien |
| 6,013,023 A | 1/2000 | Klingenstein |
| 6,030,338 A | 2/2000 | Benderev |
| 6,048,306 A | 4/2000 | Spielberg |
| 6,090,038 A | 7/2000 | Zunker et al. |
| 6,090,098 A | 7/2000 | Zunker et al. |
| 6,096,057 A | 8/2000 | Klingenstein |
| 6,110,099 A | 8/2000 | Benderev |
| 6,135,945 A | 10/2000 | Sultan |
| 6,142,928 A | 11/2000 | Zunker et al. |
| 6,216,698 B1 | 4/2001 | Regula |
| 6,319,191 B1 | 11/2001 | Sayet et al. |
| 6,418,930 B1 | 7/2002 | Fowler |
| 6,428,467 B1 | 8/2002 | Benderev |
| 6,470,890 B1 | 10/2002 | Diokno et al. |
| 6,482,145 B1 | 11/2002 | Forsell |
| 6,503,190 B1 | 1/2003 | Ulmsten et al. |
| 6,558,370 B2 | 5/2003 | Moser |
| 6,569,078 B2 | 5/2003 | Ishikawa et al. |
| 6,645,137 B2 | 11/2003 | Ulmsten et al. |
| 6,676,594 B1 | 1/2004 | Zunker et al. |
| 6,682,473 B1 | 1/2004 | Matsuura et al. |
| 6,723,040 B2 | 4/2004 | Brady |
| 6,752,754 B1 | 6/2004 | Feng et al. |
| 6,770,025 B2 | 8/2004 | Zunker |
| 6,786,861 B1 | 9/2004 | Pretorius |
| 6,808,485 B2 | 10/2004 | Zunker |
| 6,843,766 B1 | 1/2005 | Nemir et al. |
| 6,913,573 B1 | 7/2005 | Viscomi et al. |
| 6,915,165 B2 | 7/2005 | Forsell |
| 6,939,289 B2 | 9/2005 | Zunker et al. |
| 6,976,950 B2 | 12/2005 | Connors et al. |
| 7,074,178 B2 | 7/2006 | Connors et al. |
| 7,083,569 B2 | 8/2006 | Boulanger et al. |
| 7,144,391 B1 | 12/2006 | Kreutz et al. |
| 7,235,044 B2 | 6/2007 | Forsell |
| 7,258,661 B2 | 8/2007 | Davies et al. |
| 7,306,586 B2 | 12/2007 | Beaufore et al. |
| 7,311,661 B2 | 12/2007 | Heinrich |
| 7,360,544 B2 | 4/2008 | Levien |
| 7,445,598 B2 | 11/2008 | Orban, III |
| 7,540,876 B2 | 6/2009 | Connors et al. |
| 7,553,273 B2 | 6/2009 | Ferguson et al. |
| 7,628,155 B2 | 12/2009 | Carey |
| 7,628,156 B2 | 12/2009 | Astani et al. |
| 7,658,196 B2 | 2/2010 | Ferreri et al. |
| 7,673,631 B2 | 3/2010 | Astani et al. |
| 7,691,051 B2 | 4/2010 | Connors et al. |
| 7,695,427 B2 | 4/2010 | Kugler et al. |
| 7,717,892 B2 | 5/2010 | Bartning et al. |
| 7,722,583 B2 | 5/2010 | Kim et al. |
| 7,771,344 B2 | 8/2010 | Ziv |
| 7,771,346 B2 | 8/2010 | Burton et al. |
| 7,775,215 B2 | 8/2010 | Hassler, Jr. et al. |
| 7,775,966 B2 | 8/2010 | Dlugos et al. |
| 7,794,385 B2 | 9/2010 | Rosenblatt |
| 7,819,821 B2 | 10/2010 | Forte et al. |
| 7,828,713 B2 | 11/2010 | Ziv et al. |
| 7,828,714 B2 | 11/2010 | Feng et al. |
| 7,828,715 B2 | 11/2010 | Haverfield |
| 7,828,716 B2 | 11/2010 | Burton et al. |
| 7,844,342 B2 | 11/2010 | Dlugos, Jr. et al. |
| 7,892,163 B2 | 2/2011 | Bartning et al. |
| 7,927,270 B2 | 4/2011 | Dlugos et al. |
| 7,927,320 B2 | 4/2011 | Goldwasser et al. |
| 8,740,766 B2 | 6/2014 | Rosen et al. |
| 8,740,767 B2 | 6/2014 | Rosen et al. |
| 2002/0183833 A1* | 12/2002 | Stevens .......... A61F 2/07 623/1.22 |
| 2006/0025798 A1 | 2/2006 | Cook et al. |
| 2006/0130848 A1 | 6/2006 | Carey |
| 2006/0211911 A1 | 9/2006 | Jao et al. |
| 2007/0203429 A1 | 8/2007 | Ziv |
| 2008/0033231 A1 | 2/2008 | Bartning et al. |
| 2009/0111671 A1 | 4/2009 | Campbell et al. |
| 2009/0192346 A1 | 7/2009 | Rosenblatt |
| 2009/0216071 A1 | 8/2009 | Zipper |
| 2009/0266367 A1* | 10/2009 | Ziv .......... A61F 2/005 128/834 |
| 2009/0283099 A1 | 11/2009 | Harmanli |
| 2011/0015474 A1 | 1/2011 | Forsell |
| 2012/0116415 A1 | 5/2012 | Forsell |
| 2013/0012764 A1 | 1/2013 | Herbowy et al. |
| 2013/0138135 A1 | 5/2013 | Rosen et al. |
| 2013/0144112 A1 | 6/2013 | Rosen et al. |
| 2013/0150661 A1 | 6/2013 | Rosen et al. |

FOREIGN PATENT DOCUMENTS

| | | |
|---|---|---|
| EP | 0700669 | 3/1996 |
| EP | 1518514 | 3/2005 |
| EP | 1587464 | 8/2007 |
| EP | 1587465 | 11/2007 |
| EP | 160944 | 7/2008 |
| EP | 1734895 | 7/2008 |
| EP | 1734892 | 3/2011 |
| EP | 1990023 | 9/2012 |
| FR | 2843700 | 2/2004 |
| GB | 2352181 | 1/2001 |
| WO | WO1993/016659 | 9/1993 |
| WO | WO1996/001084 | 1/1996 |
| WO | WO2001/045487 | 6/2001 |
| WO | WO2002/053235 | 7/2002 |
| WO | WO2002/098323 | 12/2002 |
| WO | WO2005/082276 | 9/2005 |
| WO | WO 2007/049154 | 5/2007 |
| WO | WO2008/085825 | 7/2008 |
| WO | WO2009/046996 | 4/2009 |
| WO | WO2009/046997 | 4/2009 |
| WO | WO2009/060437 | 5/2009 |
| WO | WO2011/008167 | 1/2011 |
| WO | WO2011/116108 | 9/2011 |
| WO | WO 2011116108 A1 * | 9/2011 .......... A61F 2/0009 |

OTHER PUBLICATIONS

Sokol et al; Clinical Anatomy of the Vulva, Vagina, Lower Pelvis, and Perineum; Global Library of Women's Medicine; 14 pgs.; Sep. 2008 (printed from http://www.glowm.com/section_view/heading/Clinical%20Anatomy%20of%20the%20V on Dec. 23, 2013).

Viera et al.; Practical use of the pessary; Am Fam Physician; 61(9); pp. 2719-2726; May 1, 2000(downloaded Mar. 8, 2013 from: http://www.aafp.org/afp/2000/0501/p2719.html?printable=afp).

(56) References Cited

OTHER PUBLICATIONS

Supplemental European Search Report for Application No. EP11756942.6 dated May 29, 2017, 7 pages.

\* cited by examiner

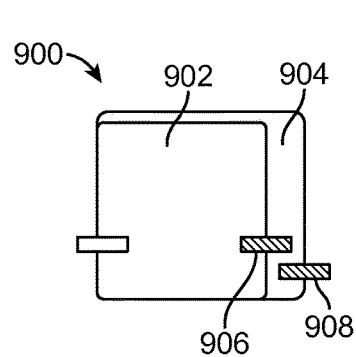 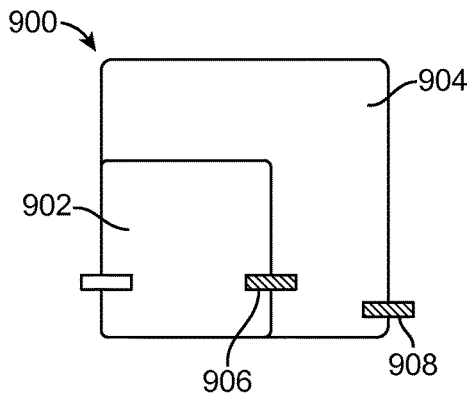
FIG. 9A  FIG. 9B
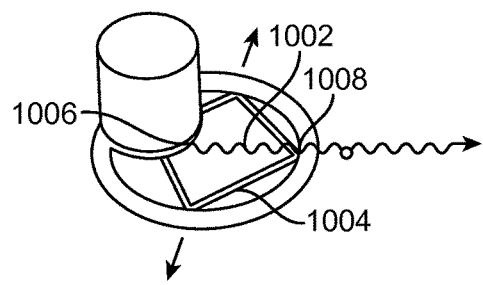 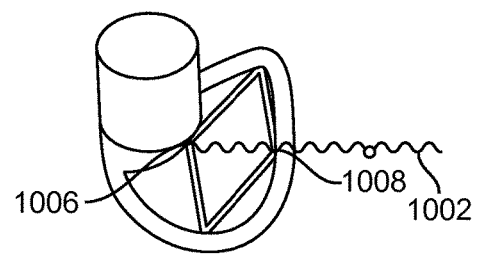
FIG. 10A  FIG. 10B

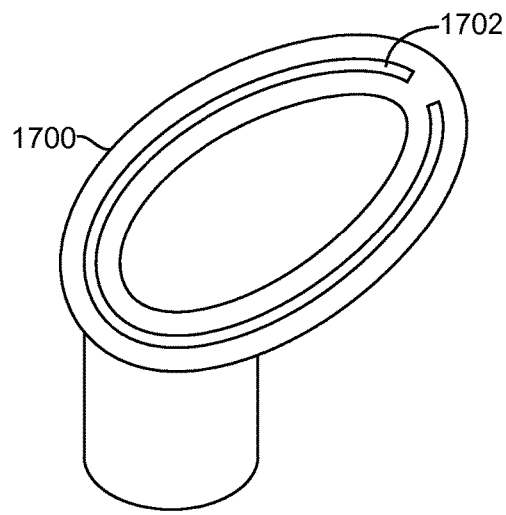
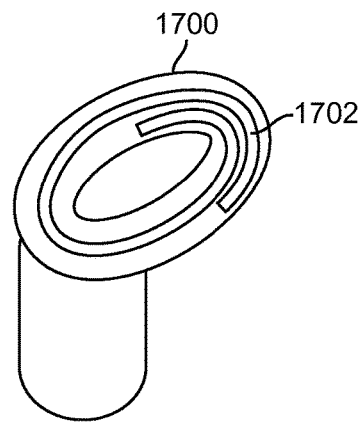
FIG. 17A          FIG. 17B
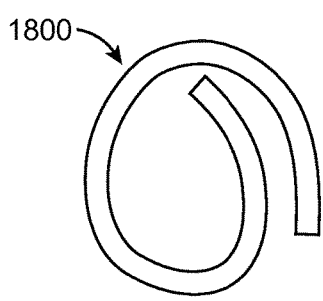
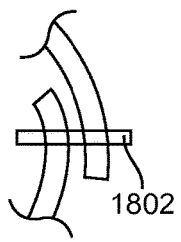
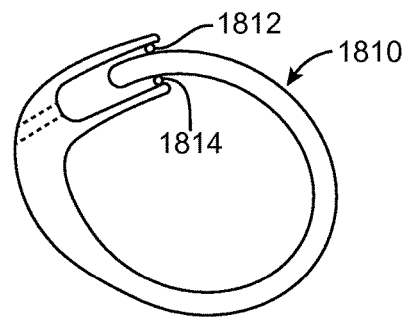
FIG. 18A          FIG. 18B          FIG. 18C
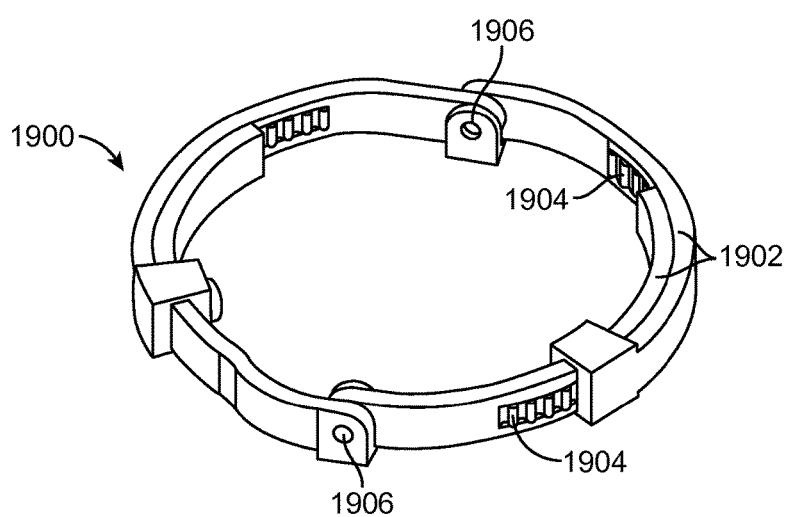
FIG. 19

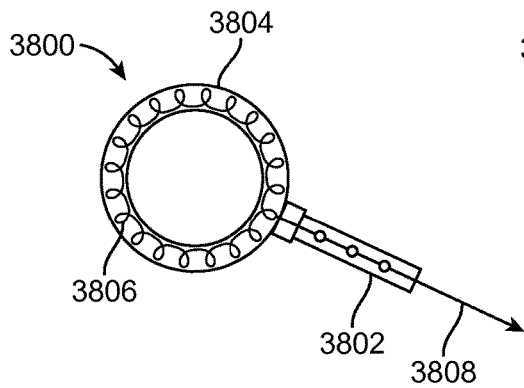
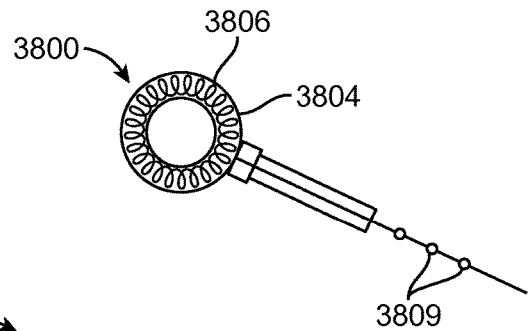
FIG. 38A
FIG. 38B
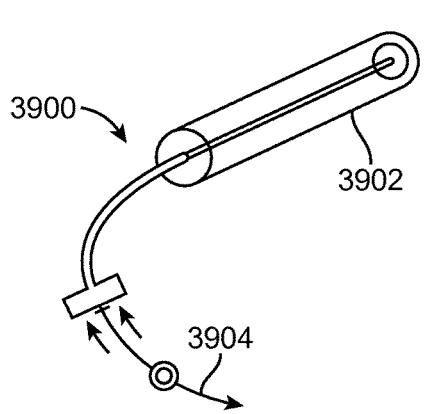
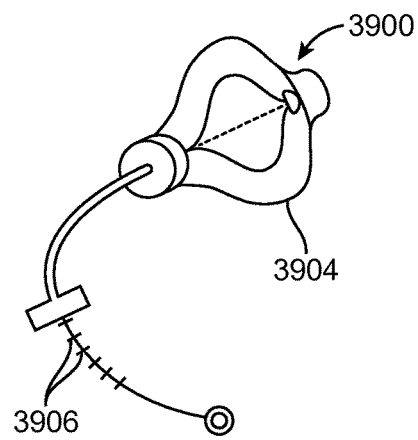
FIG. 39A
FIG. 39B
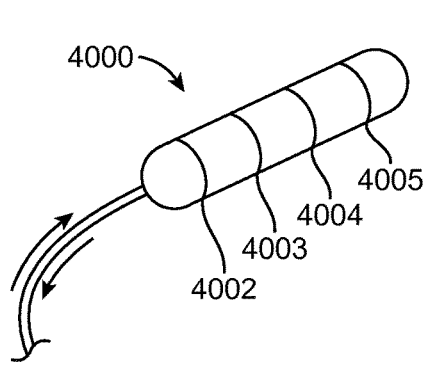
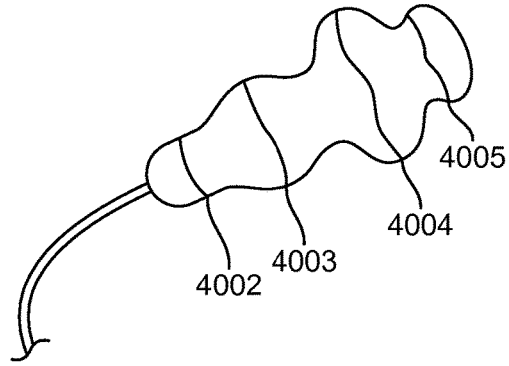
FIG. 40A
FIG. 40B

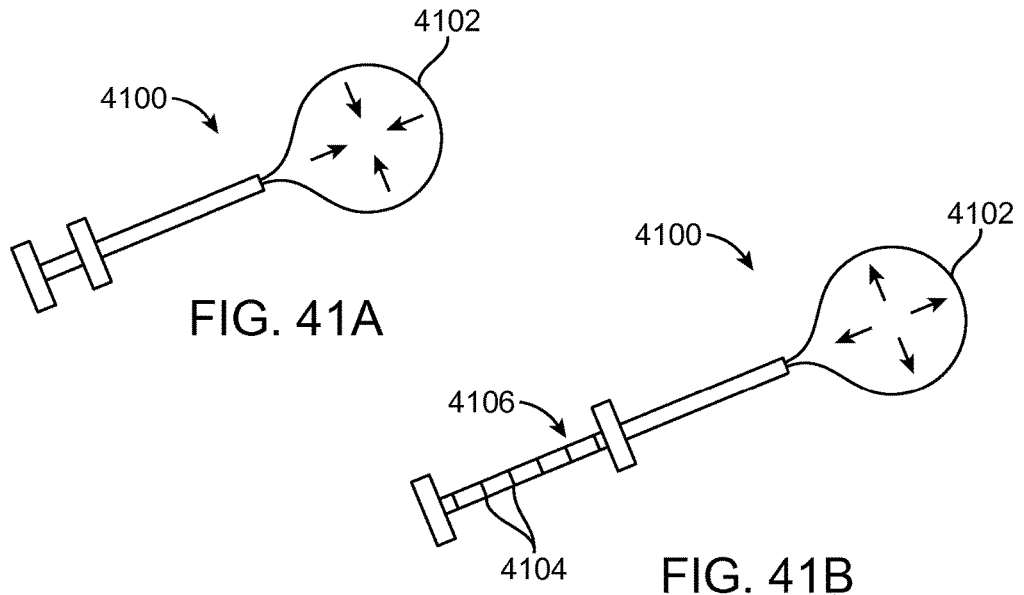
FIG. 41A
FIG. 41B
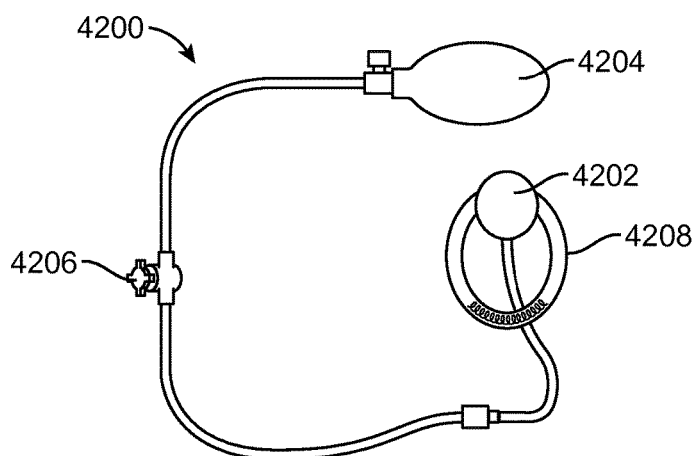
FIG. 42
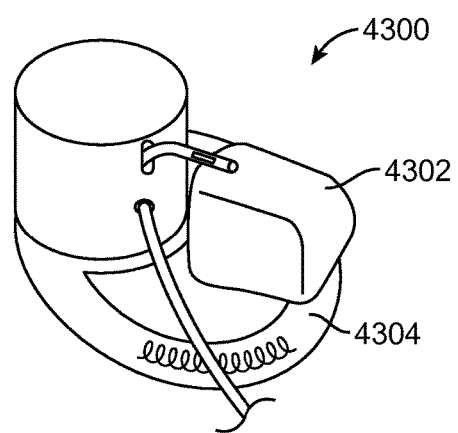
FIG. 43

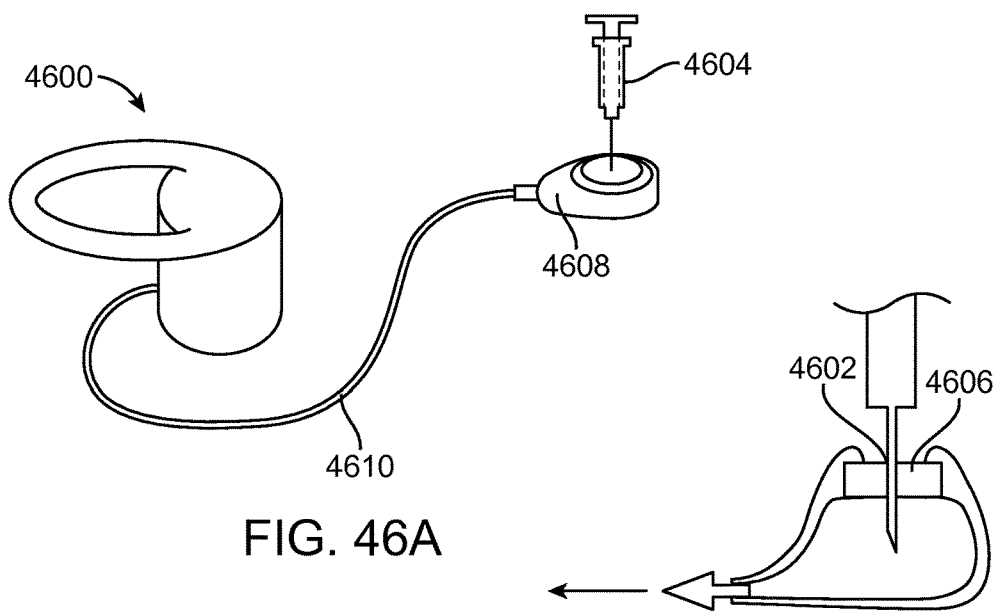
FIG. 46A
FIG. 46B
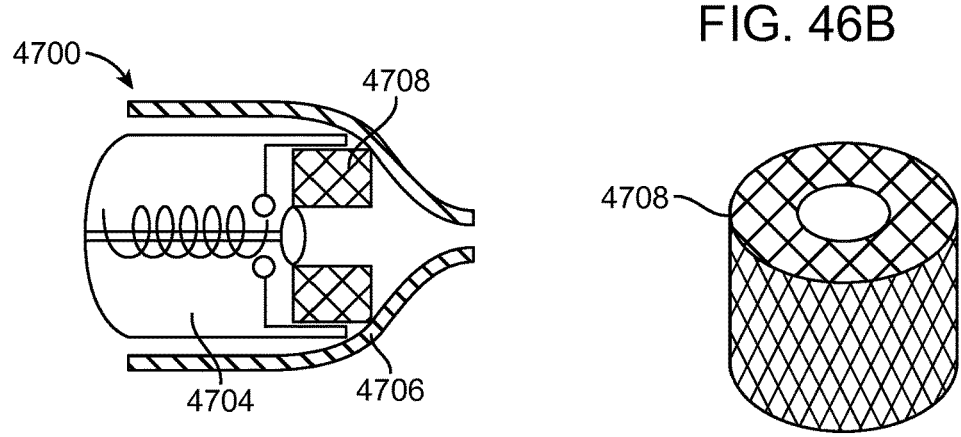
FIG. 47A
FIG. 47B
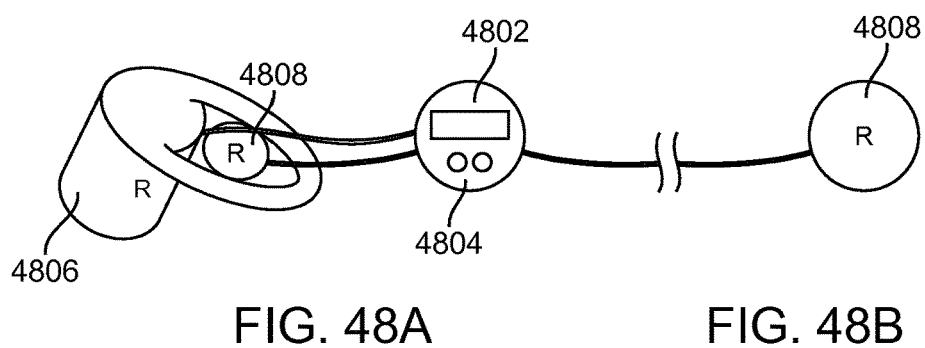
FIG. 48A
FIG. 48B

INTRA-VAGINAL DEVICES AND METHODS FOR TREATING FECAL INCONTINENCE

CROSS REFERENCE TO RELATED APPLICATIONS

This application claims the benefit of U.S. Provisional Application No. 61/764,960, filed Feb. 14, 2013, and entitled "VAGINAL BOWEL CONTROL DEVICES AND METHODS OF USE".

INCORPORATION BY REFERENCE

All publications and patent applications mentioned in this specification are herein incorporated by reference to the same extent as if each individual publication or patent application was specifically and individually indicated to be incorporated by reference.

FIELD

This application relates to the field of intra-vaginal devices for the treatment of fecal incontinence.

BACKGROUND

Fecal incontinence (FI) is one of the most common health problems in women. The prevalence of FI is not well understood, primarily because the stigma surrounding the condition and the lack of viable treatments have deterred many women from seeking medical care. Recent general population surveys indicate the prevalence of FI at 9% to 12% and as high as 24% in older women. These studies have also shown that, although prevalence increases somewhat with age, younger women have surprisingly high prevalence rates. The condition is both physically limiting and emotionally devastating. Those afflicted are often forced to withdraw from social and professional activities and often face problems in their private personal relationships.

The cause of FI is multifactorial and not completely understood. Often times, women with FI have a history of damage to the pelvic floor stemming from pregnancy and childbirth. Damage can involve the internal and external anal sphincters, pelvic floor muscles, and associated nerves (e.g., pudendal nerve). Puerperal damage to these structures may not manifest until later in life, possibly due to age-related changes in rectal sensation, compliance, and volume, in addition to further weakening of the sphincters and pelvic floor muscles. Many women with FI have multiple defects in their continence system, making effective treatment particularly difficult.

Existing treatments include conservative management, surgical procedures, and permanent implants. These treatments all have limitations in efficacy and morbidity and most of the women with fecal incontinence go untreated. There is the need for a new therapy that is low-risk and offers a high degree of benefit. Disclosed in this application is a new way of treating fecal incontinence. Described is a non-surgical intravaginal device that can protrude into the rectum and prevent accidental bowel leakage.

SUMMARY OF THE DISCLOSURE

In one aspect, an intravaginal device for the control of stool passage is provided. The device comprises an expandable occluding body; and a stabilizing body supporting the occluding body to maintain position and stability of the occluding body in the user's vagina during repeated expansions of the occluding body in an extension direction to contact the user's recto-vaginal septum to at least partially occlude the rectum. The stabilizing body has at least two states, a perimeter of the device in a first state being greater than the perimeter of the device in a second state.

In some embodiments, a width of the stabilizing body and length of the stabilizing body can be adjusted separately between the first and second state. In some embodiments, a portion of the stabilizing body to which the occluding body is attached does not change size between the first and second state. In some embodiments, the perimeter of the stabilizing body comprises a plurality of segments that are longer in the first state than in the second state. In some embodiments, the elongation of the plurality of segments is coupled to an extension that is at least one of: in the same plane as the stabilizing body, perpendicular to the direction of elongation, and directed away from the stabilizing body. The stabilizing body can comprise a plurality of arms. In some embodiments, the stabilizing body comprises 4 arms. At least two arms can be connected by a hinge. In some embodiments, the hinge constrains the arms to rotational motion in the plane of the stabilizing body. The hinge can allow angular changes between the two arms. The stabilizing body can comprise a locking mechanism configured to maintain the two arms and the hinge in a particular angular configuration. In some embodiments, all of the arms are interconnected by hinges to form a loop. At least one arm can be extendible. In some embodiments, all arms are extendible. In some embodiments, the at least one extendible arm is configured to be extended by changing an amount of overlap of segments comprising the arm. The stabilizing body can be configured to be collapsible. The device can comprise an adjustment mechanism comprising a linkage configured to expand of contract the overall perimeter of the stabilizing body. The stabilizing body can comprise an interchangeable strut extending across the device, the strut configured to control the size of the stabilizing body. The stabilizing body can comprise a malleable frame. The stabilizing body can comprise overlapping segments configured to be pulled apart or pushed together. In some embodiments, the stabilizing body comprises a malleable wire wrapped around a flexible core. The device can comprise one or more fluid reservoirs configured to allow re-distribution of fluid throughout the device. In some embodiments, the stabilizing body comprises at least two segments that can be twisted with respect to one another. At least one of the segments can be bent. In some embodiments, the stabilizing body comprises at least two segments configured to slide past one another. The stabilizing body can comprise a tensile element configured to control a distance between at least two portions of the stabilizing body. In some embodiments, the stabilizing body comprises a tensile element forming at least one loop, wherein pulling or relaxing an end of the tensile element is configured to change the size of the stabilizing body. The stabilizing body can comprise a flexible sheath comprising a plurality of small rigid elements. In some embodiments, the stabilizing body is configured to be adjustable while the device is partially folded and is not configured to be adjustable while the device is fully relaxed or fully folded. The stabilizing body can comprise a flexible stretchable base comprising a pocket configured to accommodate at least two differently sized frames. In some embodiments, the device comprises connectors proximate to the expandable body configured to connect to at least two differently sized frames. The device can comprise an internal shape memory element. In some embodiments, the stabilizing body comprises a solid band maintained in a coil, an amount of overlap within the coil configured to be adjusted. The stabilizing body can comprise at least two segments comprising interlocking teeth. The stabilizing body can comprise a plurality of interlocking pieces. The stabilizing body can comprise a cover. The occluding body can be connected to the cover.

In another aspect, a method of selectively occluding a rectum to inhibit stool passage is provided. The method comprises inserting an intravaginal device into a user's vagina, the device comprising a stabilizing body and an occluding body; engaging vaginal anatomy with the stabilizing body to stably support the occluding body; adjusting a perimeter of the stabilizing body from a first state to a second state, the first state being greater than the second state; and extending the occluding body against a recto-vaginal septum of the user during the engaging step to at least partially occlude the rectum.

In some embodiments, adjusting the perimeter of the stabilizing body comprises adjusting a distance from the occluding body to a distal portion of the device. In some embodiments, adjusting the perimeter of the stabilizing body comprises adjusting the stabilizing body to position the occluding body so that it engages the recto-vaginal septum while the stabilizing body is engaging the vaginal anatomy. In some embodiments, a position of the occluding body relative to the stabilizing body remains constant during the adjusting step. In some embodiments, adjusting the perimeter of the stabilizing body comprises adding one or more extra pieces of material to the stabilizing body.

In a further aspect, an intravaginal device is provided. The device comprises a plurality of arms interconnected by hinges, the plurality of arms comprising at least one linearly extendible and retractable arm, wherein a size of the device is adjustable via extension or retraction of the at least one extendible arm.

The device can comprise four arms. The device can be collapsible. In some embodiments, the device is configured to resist out of plane bending. The device can be planar. The device can be configured to maintain curvature at different sizes. In some embodiments, at least one hinge comprises a locking mechanism configured to prevent rotation of a first arm of the two arms about the hinge. The locking mechanism can permit the device to be locked in one or more configurations. In some embodiments, the locking mechanism comprises a latch configured to interfere with a tooth on the first segment such that the first segment is prevented from rotating. In some embodiments, the at least one extendible arm comprises two segments, an amount of overlap between the two segments configured to control extension of the at least one extendible arm. In some embodiments, a first segment of the two segments comprises gear teeth and a second segment of the two segments comprises a gear configured to rotatably engage the gear teeth. In some embodiments, a first segment of the two segments comprises an elongate member and a second segment of the two segments comprises an internal chamber fluidly connected to a port, the elongate member configured to slide within the chamber upon application of positive or negative pressure to the chamber via the port. The at least one extendible can comprise a locking feature configured to prevent relative movement between the two segments. The locking feature can comprise a tooth positioned on a first of the two segments and a plurality of pockets shaped to receive the tooth positioned along a second of the two segments. In some embodiments, the tooth is attached to a lever that can be lifted to separate the tooth from one of the plurality of pockets. In some embodiments, the locking feature comprises one or more holes on a first segment of the two segments configured to engage a feature on a second segment of the two segments. In some embodiments, the locking feature comprises a groove comprising one or more wide portions on a first arm of the two arms and a pin on a second arm of the two arms, the pin configured to slide through the groove, wherein portions of the groove other than the wide portions comprise a thickness less than a diameter of the pin. The at least one extendible arm can comprise a restraining mechanism to prevent over lengthening of the two segments. In some embodiments, the restraining mechanism comprises a slot on a first of the two arms and a pin on a second of the two arms, wherein the pin is configured to slide through the slot as the two arms move relative to one another. The two segments can comprise a rectangular or round cross-sectional profile. At least a portion of one of the two segments can be configured to slide in at least a portion of the other segment. In some embodiments, the at least one extendible arm comprises three segments, an amount of overlap between the three segments configured to control extension of the at least one extendible arm. In some embodiments, the at least one extendible arm comprises a rounding feature configured to create a rounded outer profile of the device. The rounding feature can comprise a flexible arch slidingly disposed on a ramp. The device can comprise an exterior covering. The covering can be elastomeric. The device can comprise two hinges offset from a central longitudinal axis of arms surrounding the hinges. At least two features disposed on an interior perimeter of the device can be offset from each other.

In another aspect, a method of inserting an intravaginal device is provided. The method comprises inserting the device into the vagina, the device comprising a plurality of arms interconnected by hinges, at least one arm of the plurality of arms being extendible; and adjusting a length of the at least one extendible arm, thereby changing a size or shape of the device.

In some embodiments, the adjusting step comprises locking the at least one extendible arm in an adjusted configuration. In some embodiments, the method comprises collapsing the device to a collapsible state by allowing motion at the hinges. The device can be opened after the inserting step. In some embodiments, the method comprises locking the device in an open configuration by preventing motion of at least one of the hinges.

In yet another aspect, an intravaginal device for the control of stool passage of an adult human female user is provided. The device comprises an occluding body; an intravaginal stabilizing body supporting the occluding body; a sensor positioned on the device and configured to provide data regarding a parameter; and a controller configured to receive data from the sensor.

In another aspect, an intravaginal device for the control of stool passage of an adult human female user is provided. The device comprises an expandable occluding body; and an expandable intravaginal stabilizing body supporting the occluding body having tissue engagement surfaces sized and shaped to engage with internal vaginal anatomy to maintain position and stability of the occluding body in the user's vagina during repeated expansions of the occluding body in an extension direction to contact the user's rectovaginal septum proximal to the perineal body to at least partially occlude the rectum.

In a further aspect, a tool configured to measure a dimension of a vaginal cavity is provided. The tool comprises a head configured for insertion into the vaginal cavity, the head configured to expand when inserted in an area of the vaginal cavity to be sized; and a handle configured to indicate an amount of expansion of the head. The tool can include a portion for pressing against the rectovaginal septum. The tool can be configured to measure a lateral width of the vaginal cavity simultaneous to creating a protrusion of the posterior vaginal wall into the rectal space.

In another aspect, a method of measuring a dimension of a vaginal cavity is provided. The method comprises inserting a tool into the vaginal cavity, the tool comprising a head and a handle; expanding the head of the tool within the vaginal cavity using a desired amount of force; and observing the amount of expansion of the head by viewing markings on the handle.

In some embodiments, the tool includes a portion for pressing against the rectovaginal septum. In some embodiments, the tool is configured to measure a lateral width of the vaginal cavity simultaneous to creating a protrusion of the posterior vaginal wall into the rectal space.

In a further aspect, a tool configured to measure a dimension of a vaginal cavity is provided. The tool comprises a head configured for insertion into the vaginal cavity, the head configured to expand when inserted in an area of the vaginal cavity to be sized; one or more sensors positioned on the head and configured to provide data regarding a parameter; and a controller configured to receive data from the one or more sensors and use the data to determine a dimension of the vaginal cavity.

In yet another aspect, an intravaginal device for the control of stool passage of an adult human female user is provided. The device comprises an expandable occluding body; and an intravaginal stabilizing body supporting the occluding body having tissue engagement surfaces sized and shaped to engage with internal vaginal anatomy to maintain position and stability of the occluding body in the user's vagina during repeated expansions of the occluding body in an extension direction to contact the user's rectovaginal septum proximal to the perineal body to at least partially occlude the rectum, the stabilizing body molded from at least a portion of an interior of the user's vaginal cavity.

In another aspect, a method of creating an intra-vaginal device is provided. The method comprises inserting a bladder in a vaginal cavity of a patient; filling the bladder with foam to a desired volume or pressure; and curing or hardening the foam in place, creating a cast of the vaginal cavity. The method can comprise removing the cast from the vaginal cavity and adding additional structural elements to the cast.

In a further aspect, a pump for use with an intravaginal device is provided. The pump comprises a compressible body configured to pump air from within the body to an output upon compression of the body; and a relief valve configured to release air upon the device pressure exceeding a predetermined limit, wherein airflow to the relief valve is configured to be suppressed during compression.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A-B illustrate an embodiment of an adjustable occluding body.

FIGS. 10A-B illustrate an embodiment of an adjustable intra-vaginal device.

FIGS. 17A-B illustrate an embodiment of an adjustable intra-vaginal device.

FIGS. 18A-C illustrate an embodiment of an adjustable intra-vaginal device frame.

FIG. 19 illustrates an embodiment of an adjustable intra-vaginal device frame.

FIGS. 38A-B illustrate an embodiment of a sizing tool.

FIGS. 39A-B illustrate an embodiment of a sizing tool.

FIGS. 40A-B illustrate an embodiment of a sizing tool.

FIGS. 41A-B illustrate an embodiment of a sizing tool.

FIG. 42 illustrates an embodiment of an occluding body stand-in system.

FIG. 43 illustrates an embodiment of a fitting tool.

FIGS. 46A-B illustrate an embodiment of a pump.

FIGS. 47A-B illustrate an embodiment of a relief valve.

FIGS. 48A-B illustrate an embodiment of an intra-vaginal device and pump.

DETAILED DESCRIPTION

Figure 1A:
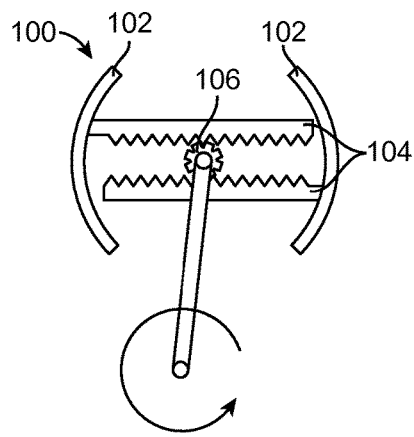
FIGS. 1A and B illustrate an embodiment of an adjustment mechanism.

The disclosure herein relates generally to intra-vaginal devices and methods for controlling the passage of stool. The devices are adapted to at least partially occlude the rectum to control the passage of stool while remaining stable inside the vagina.

Extensive cadaver testing and human clinical testing and trials were performed in order to understand key attributes for devices that will achieve the desired vaginal bowel control (VBC). First, the ability to achieve rectal occlusion was found to be influenced by a variety of design features that were unanticipated from knowledge of the anatomy. Second, the stability of the device not only during rectal occlusion but also when the device is not occluding the rectum turned out to be a key aspect of device function and required specific adaptations to ensure the device is stabilized when it is not occluding and when it is occluding. Finally, the devices have to be adapted to interact with the tissue in a way that is comfortable and safe to the user while achieving occlusion and stability. Through bench and human clinical testing, these discoveries of how device design impacted device performance including rectal occlusion, device stability, and user safety and comfort, led to the development of inventive and effective vaginal bowel control devices.

While the disclosure herein focuses on the control of stool passage to treat FI, the devices, systems, and methods of use herein can be used or adapted to be used in one or more other bowel control applications, such as in, for example, the treatment of irritable bowel syndrome ("IBS"), strong urgency to have a bowel movement, diarrhea, loose stools, frequent bowel movements, flatal incontinence, constipation, hard stools, irregular or infrequent bowel movements, abdominal pain or discomfort, cramps, bloating, incomplete stool evacuation, and rectoceles. By compressing the rectum, the device may mitigate the urge to have a bowel movement that comes from a distended rectum, or via some related neurological feedback disruption. In reducing the urge or mechanically blocking stool from passing, it may also increase absorption of liquids from the stool passing through the GI tract, causing less frequent stools and stools that are not as loose in nature. Since these symptoms are often associated with abdominal pain or discomfort, especially in patients with IBS, the devices may help with those symptoms. The devices may also help women become more regular if they are constipated or have hard stools by compressing and decompressing the rectum, thereby applying a regular stimulus that can encourage stool passage. In patients who have a rectocele where stool collects and they may not completely evacuate, the devices can correct the rectocele or deflect it back into a position where stool can exit normally. Additionally, the devices herein can be used or adapted to be used in the treatment of gastrointestinal conditions that may be related to bowel habits or colon and rectum function, for example diverticulitis, hemorrhoids, anal fissures.

One aspect of the disclosure is an intra-vaginal device for the control of rectal volume of an adult human female user, the device comprising a rectal compressing portion and a stabilizing portion, wherein both portions being sized and configured to maintain position and stability while fitting entirely within the vagina and compressing the rectum. Previous attempts have failed to describe or teach an entirely intra-vaginal device designed for stably compressing the rectum.

In this disclosure, the rectal compressing portion may also be referred to as an occluding portion or a force applying portion, and similarly, the act of compressing the rectum may also be referred to as occluding the rectum or applying a force towards the rectum. While most embodiments described herein are described as reversibly occluding, or having occluding and non-occluding states, it is possible for a device in a non-occluding state to still apply some small amount of force on the rectovaginal septum, creating a minor deflection or occlusion of the rectum. However, any such minor forces are inconsequential for the effects on the bowels described herein. A stabilizing body herein could also be referred to as a stabilizing portion. The stabilizing portion and occluding portion are not necessarily different parts, but rather aspects of the device named here for convenience of description. It is the design and configuration of the devices as a whole (including the configuration of the stabilizing and occluding portions and their relationship to each other) that produces the stability, occlusion, and comfort necessary for function.

One aspect of the disclosure is a rectal compressing portion that is extendable or expandable, allowing it to reversibly compress the rectum. The device is an intravaginal device adapted to maintain position and stability in both extended and non-extended states. One of the drawbacks with previous attempts at stool control is that they fail to teach or describe devices that are intra-vaginally stabilized when an expandable portion is in a non-extended state. One of the advantages of the devices herein is that they are sized and configured to stabilize and maintain the device in a desired orientation when the occluding portion is in a non-occluding state. Additionally, the devices are sized and configured to stabilize and maintain the device in the desired orientation throughout repeated changes between occluding configurations and non-occluding configurations. Additionally, the devices are sized and configured to cause the occluding portion to repeatedly extend against the rectovaginal septum in a desired extension direction to at least partially occlude the rectum even after the occluding portion has transitioned to a non-occluding state. Additionally, the devices are sized and configured to extend against the same part of the recto-vaginal septum, and as later described, the location on the rectovaginal septum where the portion extends is important. Additionally, the devices are sized and configured to maintain the occluding portion extended against, and in a position where it can be readily extended against, rectovaginal septum in extended and non-extended states, respectively.

It has been discovered through testing that how the device is designed to engage and be positioned within the surrounding anatomy is important for stabilizing the device and occluding the rectum. One aspect of this disclosure is a device configured to fit proximal to the area of the pubic ramus in order to stabilize the device when the occluding portion is extended and non-extended. Vaginal bowel control devices designed and configured to engage the anatomy as described allow for increased stability when the occluding portion is in extended and non-extended states. It is further described below how the device is designed and configured to engage the surrounding internal vaginal anatomy for stabilization in occluding and non-occluding states.

Through the course of experimentation, another important discovery was to compress the rectum proximal to the perineal body. During human clinical testing, it was more difficult to obtain intravaginal rectal occlusion with the same posterior force application in the area of the perineal body than in the area proximal to the perineal body. This result was unanticipated because the rectal canal is narrower in the region of the perineal body. Users also felt greater discomfort when force was applied to the perineal body as compared to proximal to the perineal body. Therefore, one aspect of this disclosure is a device designed and configured to stably and repeatedly compress the rectum proximal to the perineal body. This development, as a result of clinical findings, is different than might be suggested based on other mechanisms in medical devices for bowel control. For example, the Acticon® Neosphincter, which also compresses the anorectal canal to control stool passage, is placed at the level of the perineal body.

It was also discovered through cadaver and human clinical testing that the device's effect on surrounding vaginal tissue affects the ability of the device to occlude the rectum. More specifically, if too much slack or redundancy is taken out of the surrounding vaginal tissue by a device distending the vaginal tissue, it makes it more difficult for the device to occlude the rectum. Furthermore, it was found to be less comfortable for the user if the device compresses the rectum when the slack has been taken out of the vaginal tissue. In addition to discomfort, this places additional strain on the tissue and could lead to pressure ulceration, necrosis, or other adverse events. The discovery of this relationship in the tissue resulted in a variety of design features in the devices herein. One aspect of this disclosure is a device designed and configured to minimize the stretch to the vaginal tissue while maintaining stability and compressing the rectum posteriorly. The balance of configuring a device to be stable in the vagina but also reducing stretch on the surrounding tissue in order to occlude the rectum was an important design development. Previous attempts have not described a vaginal device for stool control that is designed to maintain sufficient slack in the vaginal tissue. Additionally, it was found to be important to reduce the stretch on the surrounding vaginal tissue in proximity to the extendable portion during rectal compression.

A variety of device features were developed in order to minimize the stretch to the vaginal tissue while maintaining stability and compressing the rectum posteriorly. Such features, described in further detail below, include the dimensions of the stabilizing body, dimensions of the occluding portion, and the relationship between the dimensions of the stabilizing body and occluding portion; as well as their positioning, absolute and relative to each other.

One aspect of this disclosure is a device designed and configured with a flattened stabilizing portion in relation to the occluding portion. More specifically, the stabilizing body is flattened in a direction substantially perpendicular to the direction of occluder extension. More specifically, the stabilizing portion has a thickness less than the length of the occluding portion. In this disclosure, a flattened stabilizing portion can also be described as: a portion whose thickness in the direction perpendicular to its lateral span and local longitudinal axis is less than the lateral span; particular range of width, length and thickness ratios describing a reduced thickness; a cross-sectional profile (taking the cross-sectional cut with a plane normal to the longitudinal axis of the device, or a plane normal to the proximal-distal axis of the vagina when the device is in-situ) that is relatively short, compared to its width; or a generally planar shape. The elements of such a profile are important for several reasons that were discovered through clinical testing. A stabilizing portion that is flattened relative to the occluding portion, and more specifically in a direction substantially perpendicular to the direction of extension of the occluding portion, provides enough slack in the vaginal walls in order to allow the extendable portion to better and more comfortably compress the rectum. This is in contrast with work disclosed in the prior art attempts, some of which describes a bulky, tubular base. At the same time, a flattened stabilizing portion with appropriate dimensions was also found to contribute to device stability by resisting rotation and translation from forces generated by rectal occlusion, as described further below. A flattened stabilizing portion relative to a direction of extension of the occluding portion also allows the device to fit in the area between the pubic ramus and the posterior fornix. More specifically, it allows the distal end of the device to fit anteriorly in the area of the pubic notch. The positioning that is achieved based on the design contributes to device stability by keeping it snug to the surrounding tissue and better occlusion by helping keep the occluding portion proximal to the perineal body.

Exemplary intra-vaginal devices and methods are described in U.S. Publication No. 2013/0150661 (application Ser. No. 13/625,683), filed Sep. 24, 2012, entitled "INTRA-VAGINAL DEVICES AND METHODS FOR TREATING FECAL INCONTINENCE"; U.S. Publication No. 2013/0138135 (application Ser. No. 13/679,484), filed Nov. 16, 2012, entitled "INTRA-VAGINAL DEVICES AND METHODS FOR TREATING FECAL INCONTINENCE"; U.S. Publication No. 2013/0144112 (application Ser. No. 13/679,528), filed on Nov. 16, 2012, entitled "INTRA-VAGINAL DEVICES AND METHODS FOR TREATING FECAL INCONTINENCE"; International Publication No. WO 2011/116108 (Int'l. App No. PCT/US2011/028691), filed on Mar. 15, 2011, entitled "INTRA-VAGINAL DEVICE FOR FECAL INCONTINENCE"; and International Publication No. WO 2013/044239 (Int'l App. No. PCT/US2012/056923), filed Sep. 24, 2012, entitled "INTRA-VAGINAL DEVICES AND METHODS FOR TREATING FECAL INCONTINENCE", the disclosures of which are incorporated herein in their entireties.

Adjustable Devices

In some embodiments, an adjustable intra-vaginal device is provided. Adjustable intra-vaginal devices can be configured to adjust to comprise perimeters of different sizes. Different patients may have vaginal anatomies that vary in size or shape. Instead of providing devices in multiple sizes, a single device is capable of assuming various sizes. Such an adjustable device would allow clinicians to stock fewer devices while still being able to cater to a varying patient population. An adjustable device may have an increased likelihood of correctly fitting a patient, as the different shapes and sizes it can be adjusted to may better match a patient's anatomy. Additionally, in some patients, a device may need to be inserted to determine whether the fit is proper. In this case, an adjustable device would allow for the same device to be adjusted if it is not a good fit instead of requiring a new device to be used and requiring disposal or re-processing of the initial device. Additionally, if patient anatomy changes during the use period, an adjustable device could advantageously provide an increased likelihood of maintaining a correct fit for the patient.

The proper location and positioning of the occluding member for a vaginal device for fecal incontinence can be important for successful treatment, as outlined above. Additionally, the proper shape of the device, and the relative shapes and sizes of the stabilizing body and occluding portion can be important for successful treatment, as outlined above. Therefore the use of adjustable features to better suit a device to the anatomical needs of patients is an important development in vaginal devices for fecal incontinence.

Adjustable devices may be adjusted through the use of external tools that can be inserted into the vagina. The tools can engage with the device to adjust the adjustability mechanism. In some embodiments, patients and physicians can adjust the device. In some embodiments, adjustments are made only by the physician, with or without particular tools.

Figure 1B:
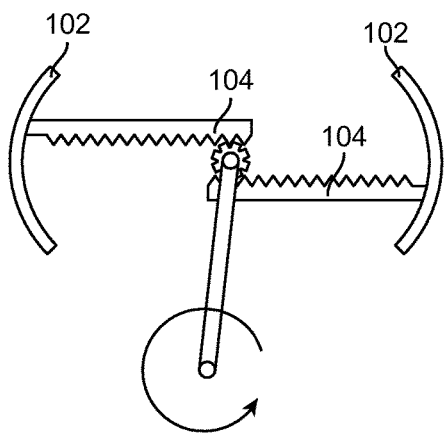

FIG. 1A illustrates an embodiment of an adjustment mechanism 100 comprising a linkage that can be used to expand or contract the overall perimeter of the device through the application of force. The mechanism 100 comprises arms 102 configured to push on a perimeter of the device. FIGS. 1A and 1B illustrate two arms, but more arms are also possible. The mechanism 100 comprises linkages 104 that are translated with respect to one another using a gear 106. In some embodiments, a screw can be used to translate linkages 104. FIG. 1B illustrates the linkages 104 being driven to spread the arms 102. Adjustment mechanism 100 can be used as an external tool to adjust the size of an adjustable intra-vaginal device or can be provided on the device itself. In some embodiments, other screw mechanisms (e.g., a hose clamp) can be used to drive opposing elements and create changes in size.

Figure 2A:
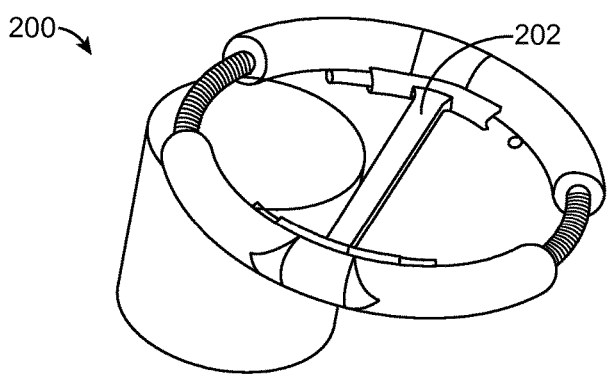
FIGS. 2A and B illustrates an embodiment of an adjustable intra-vaginal device.
Figure 2B:
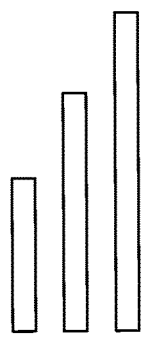

FIG. 2A illustrates an embodiment of a device 200 comprising a strut 202 extending across the device. The device 200 can use interchangeable struts of different sizes and shapes to expand or contract an adjustable device frame. The device frame can be configured to adjust the frame perimeter (e.g., by stretching, by a detent-style mechanism between sliding arms, or the like). FIG. 2B illustrates embodiments of variously sized struts that can be used with the device 200.

Figure 3A:
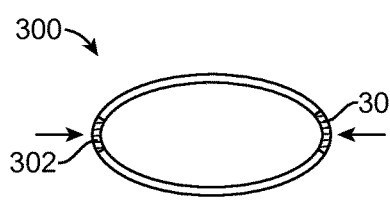
FIGS. 3A-E illustrate another embodiment of an adjustable intra-vaginal device.
Figure 3B:
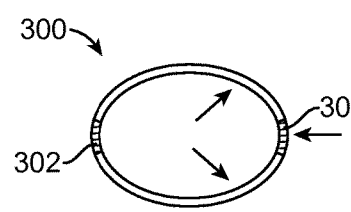
Figure 3C:
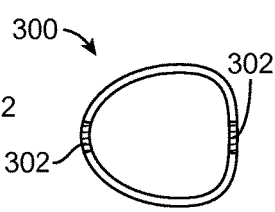
Figure 3D:
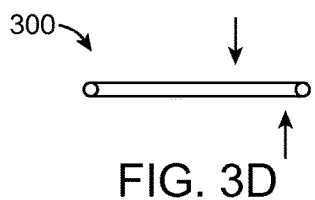
Figure 3E:
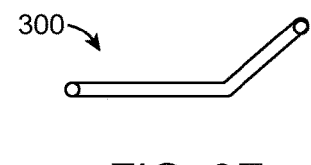

FIG. 3A illustrates an embodiment of a malleable device frame 300. The frame 300 can be manually adjusted to achieve a better fit. Alternatively, the frame 300 can be adjusted via the use of a tool. In some embodiments, the frame 300 includes hinges 302 that can be used to fold the device 300 for easier insertion and removal, as shown in FIG. 3A. FIG. 3B illustrates the frame 300 after its shape has been changed. The length has been increased while the width has been decreased. FIG. 3C illustrates the frame 300 formed into a custom shape. As shown in FIG. 3C, in some embodiments, the device 300 can be adjusted to include special curvatures to interact with vaginal anatomy for stabilization. FIG. 3D illustrates a side view of the frame 300 being bent as indicated by the arrows to form the custom shape shown in FIG. 3E. As depicted here, the custom shape includes a bend that is out of the plane of the device. Custom shapes within the plane of the device are also possible.

In device embodiments configured to expand, such as that shown in FIGS. 2A and 2B, extra material, or more specifically, loops of extra material, can be built into the initial shape to allow for grater expandability. In some embodiments, the extra material or loops are concentrated in specific locations. In some embodiments, the extra material or loops are distributed around the device.

In some embodiments, the ability to change the shape of the device may be provided by a plurality of ball and socket segments. Such segments can allow for shape adjustment of the device by permitting the repositioning of the orientation of the ball within the socket on one or more joints. In some embodiments, the ball and socket joints are passively resistant to movement by friction. In some embodiments, the ball and socket joints are actively loosened for adjustments and tightened to secure the shape of the device. Additional ball and socket joints can be added to increase the overall size of the device. Ball and socket joints can be removed from the device to reduce the overall size of the device.

Figure 4A:
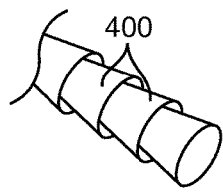
FIGS. 4A-C illustrate an embodiment of a frame of an adjustable intra-vaginal device.
Figure 4B:
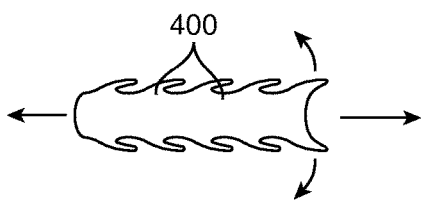
Figure 4C:
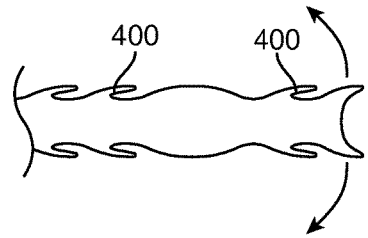

FIG. 4A illustrates an isometric view of an embodiment of a portion of a device frame comprising overlapping segments 400 similar to the bendable portion of a drinking straw. The overlapping segments can create friction and stability, or allow for re-positioning via their geometry providing for multiple stable states. FIG. 4B illustrates a side view of the overlapping segments 400. When the segments 400 are pulled apart, as illustrated in FIG. 4C, the device can become longer or more flexible. When the segments are pushed together, the device can become stiffer or softer.

Figure 5A:
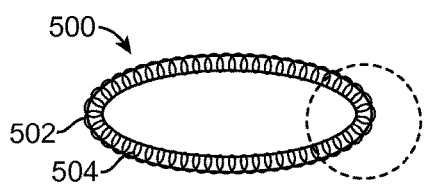
FIGS. 5A-5C illustrate an embodiment of frame of an adjustable intra-vaginal device.
Figure 5B:
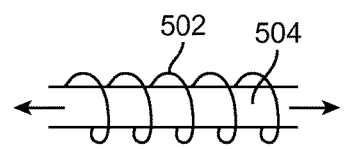
Figure 5C:
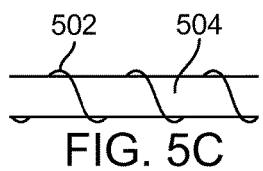

FIG. 5A illustrates an embodiment of a device frame 500. The device frame 500 comprises a malleable wire 502 wrapped around a flexible core 504. Tension can be applied to the device to expand the device. FIG. 5B illustrates a more detailed view of the core and wire moving from an unexpanded to an expanded configuration. FIG. 5C illustrates a detailed view of the core 504 and wire 502 in an expanded configuration. As the frame is stretched, the coils of the malleable wire can tighten. The core helps to ensure even stretching of the coil, distributes stress and stiffness, and reduces the risk of kinking.

Figure 6A:
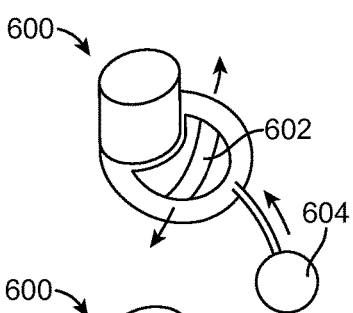
FIGS. 6A-6D illustrate embodiments of adjustable intra-vaginal devices.
Figure 6B:
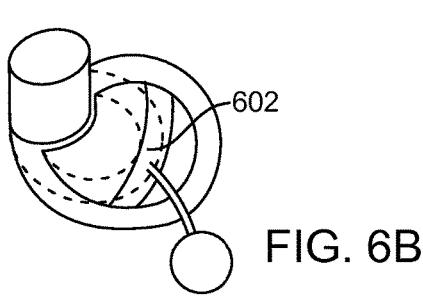
Figure 6C:
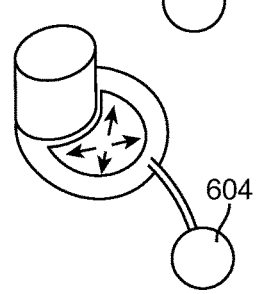
Figure 6D:
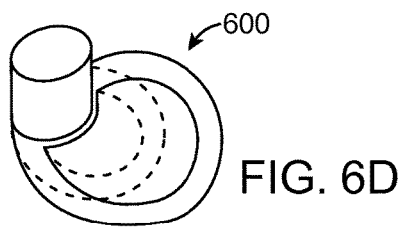

FIG. 6A illustrates an embodiment of an adjustable device 600. The device 600 comprises fluid reservoirs that can be used to drive expansion of the device 600. The fluid from a reservoir (e.g., an external reservoir) can be re-distributed throughout the device, changing and/or expanding the shape of the device. In FIG. 6A, the device 600 includes a cross-member 602 in fluid communication with an external reservoir 604. Addition of fluid from the reservoir 604 to the cross-member 602 causes the device 600 to change shape by extending the cross-member 602 which pushes on the perimeter of the device, causing it to expand, as shown in FIG. 6B. FIG. 6C illustrates an embodiment of device 600 in which the external reservoir 604 is in fluid communication with the frame of the device itself. Addition of fluid from the reservoir to the device causes the device to change shape differently from the device with the cross-member 602. In FIG. 6D, fluid is distributed throughout the device frame causing an expansion of the device frame along the path of its perimeter, increasing the overall size. To exemplify this expansion, a circularly shaped device is shown in FIG. 6D, wherein the circumference increases as the frame expands; however, other rounded shapes are possible as well.

Figure 7A:
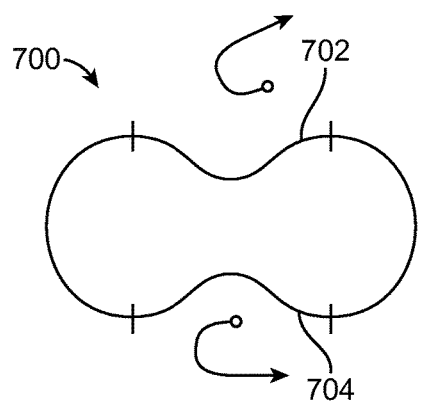
FIGS. 7A-B illustrate an embodiment of an adjustable intra-vaginal device.
Figure 7B:
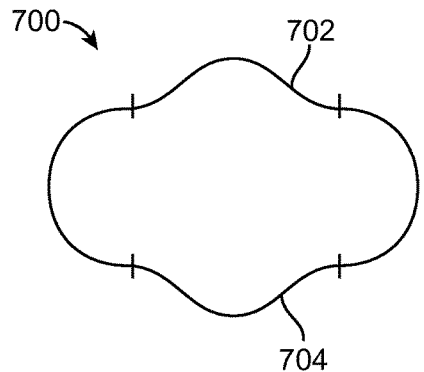

In some embodiments, the device frame can include bent or shaped segments which can be rotated or twisted with respect to each other to change the overall shape of the device. FIG. 7A illustrates an embodiment of a device frame 700 that comprises curved portions 702, 704 that can be rotated to change the shape of the device frame 700. FIG. 7B illustrates the device frame 700 after rotation of the curved portions 702, 704 in the directions indicated by the arrows. As shown in FIG. 7B, the overall shape of the frame 700 has changed, increasing in width and area.

Figure 8A:
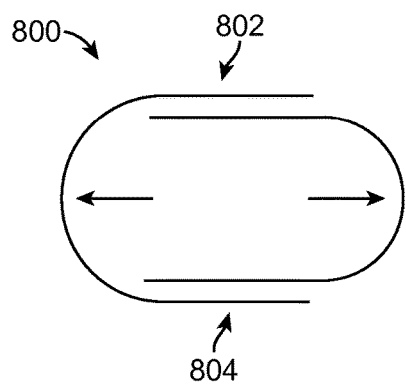
FIGS. 8A-B illustrate an embodiment of an adjustable intra-vaginal device.
Figure 8B:
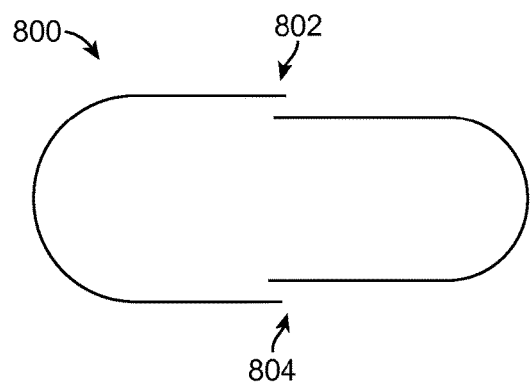

FIG. 8A illustrates an embodiment of a device frame 800 comprising regions 802, 804 that can slide past one another to increase or decrease the length of a section of the frame. FIG. 8B illustrates the device frame 800 after the regions 802, 804 have been extended, increasing the length of the frame 800. The regions 802, 804 can be manipulated via external force (e.g., manually, using a tool, using a tensile element). The regions 802, 804 can exist in a locked state or an unlocked state depending on desired initial and final dimensions of the device frame.

In some embodiments, the expandable body may provide adjustability to the device. In some embodiments, an adjustable device frame can be configured to ratchet or deform open or expand upon activation of the expandable body. The opening or expansion of the frame may stop when the opening force is balanced with the force applied by the patient anatomy or when expansion stops. In some embodiments, the device retains it shape after un-expanding the expandable body. The expansion of the frame can also be reversible, for example, by unlocking the ratcheting mechanism. Alternately, or together with a mechanical means (such as unlocking a ratcheting mechanism), the expansion of the frame can be reversible by un-expanding the expandable portion.

In some embodiments, the expansion of the expandable body may drive a spring force mechanism, or a constant-force spring mechanism expanding the device frame. In such embodiments, when expansion is reversed, the device frame can also shrink.

FIG. 9A illustrates an embodiment of an adjustable expandable body 900. Shown in FIGS. 9A and 9B as a cross-section, the expandable body comprises a first chamber 902 and a second chamber 904 separated by a pressure based relief valve 906. At low pressure, only the first chamber 902 fills. If a larger expandable body 900 is desired, additional pressure can be added which will trigger the relief valve 906 to open allowing the second chamber 904 to fill, as shown in FIG. 9B. For example, the first chamber 902 can be filled at about 80 mm Hg. The relief valve 906 can allow transmission of fluid when pressure greater than 90 mm Hg is applied. Filling the second chamber 904 increases the overall size and volume of the expandable body 900. The second chamber 904 may also include a relief valve 908. The relief valve 908 may open to exhaust, for example, when more than about 130 mm Hg is applied. The relief valve may also be used to empty the expandable body by applying vacuum sufficient to overcome it and therefore also the valve between the chambers. The relief valve may also be a port that is opened and closed via a valve either at the site of the port or on another extension such as a tube. Though illustrated for clarity in cross-section as a rectangular chamber, such a body could take on a number of shapes including round, rounded cylindrical, domed, toroidal, and disc shaped. In other embodiments, three or more chamber may be used, with the additional chambers being, for example, in serial. In other embodiments, 3 or more chambers may be used, consisting of two or more pathways through the device, so that specific shapes may be created, for example a device with one initial chamber that feeds to two others that are not connected directly to one another. In this example, the two chambers can fill on opposite sides of the initial chamber, creating a shape that is more oblong.

While FIGS. 9A and B, described above, describe a particular embodiment for changing the shape or size of the occluding portion, other means for changing the occluding portion's size or shape are considered as well. Examples include detachable occluding portions of different sizes and expandable occluding portions such as balloons that stretch to different shapes or sizes with changing amounts of fluid.

FIGS. 10A and B illustrate a device 1000 comprising a tensile element 1002 (e.g., wire, cord, etc.) that can be used to decrease or increase device size by expanding structural elements within the device 1000. For example, FIG. 10A illustrates an internal structure 1004 within the device frame; the tensile element 1002 passes through a distal point 1006 on the device frame and connects to a proximal point 1008 on the device frame. Tension can then be applied to the tensile element 1002, and a resistance (a force opposite the direction of tension) applied near distal point 1006. This tension draws the proximal point 1008 towards the distal point 1006, shortening the length of the device and increasing its width, as shown in FIG. 10B. The internal structure can comprise a frame as shown in FIGS. 10A and B. This frame can help maintain the planar orientation of the device by constraining motion to within the plane. This is possible, for example by the use of hinge joints joining the corners of the frame; said hinge joints together constraining motion at the joints to within the plane. The shape of the device can be changed until the anatomy resists further expansion, or expansion can be continued or stopped based on sensation from the patient (e.g. expanding until the expansion is felt, or felt to a particular degree by the patient). A friction mechanism (e.g., a slip knot or tight aperture through which the tensile element passes) can be used to fix the tensile element to the frame at a particular point along the length of the tensile element, thereby maintaining the device shape.

Figure 11A:
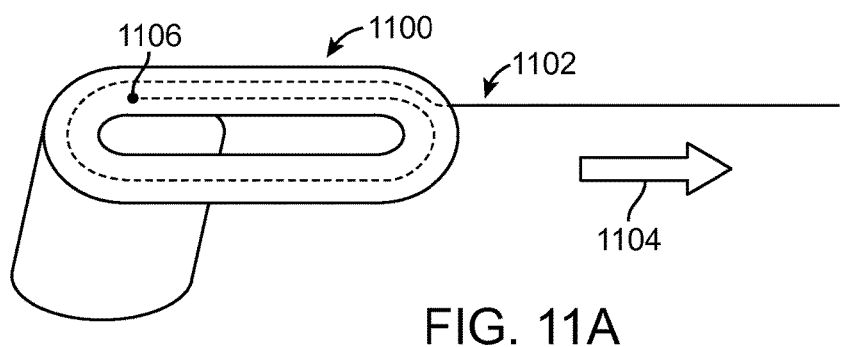
FIGS. 11A-B illustrate an embodiment of an adjustable intra-vaginal device.
Figure 11B:
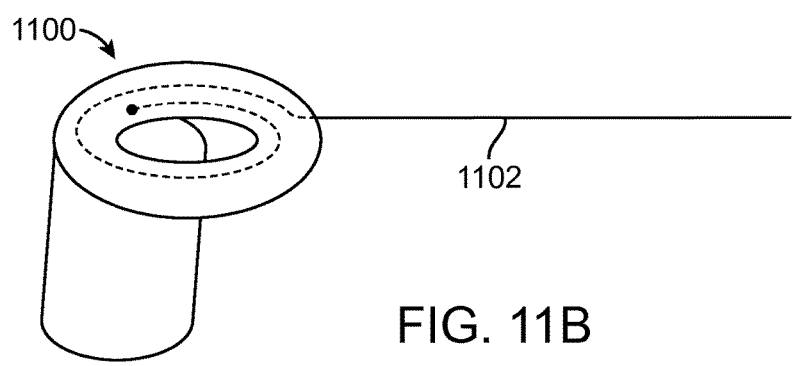

FIG. 11A illustrates a device with a stabilizing body 1100 also comprising an element 1102 configured to change the device size. As shown in FIG. 11B, the element 1102 can be pulled on in the direction of arrow 1104 to decrease the size of the stabilizing body 1100. For example, element 1102 can be a tensile element such as a string or wire that resides within the stabilizing body, forming at least one loop; one end 1106 of the element 1102 is fixed to stabilizing body 1100. When element 1102 is tensioned, it tightens the loop, thereby changing the shape of stabilizing body 1100, as shown in FIG. 11B. Element 1102 can also have some rigidity itself and even provide radial strength when in a loop; for example, element 1102 can be a wire or a band of material with some resilience that at rest is straight, or has a very large radius of curvature. In this example, when coiled, the resulting structure would have some radial strength. In some embodiments, it is also possible to push element 1102 to increase the size of the stabilizing body.

Figure 12A:
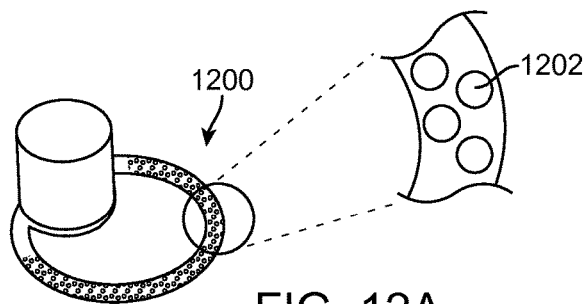
FIGS. 12A-B illustrate an embodiment of an adjustable intra-vaginal device.
Figure 12B:
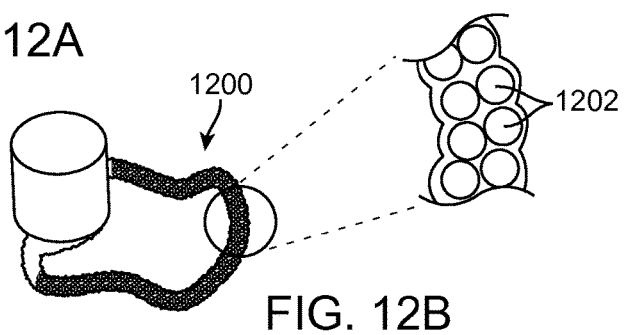

FIGS. 12A and B illustrate an embodiment of a device comprising a sheath 1200 that is flexible, the sheath 1200 comprising a plurality of small rigid elements 1202 (e.g., beads). The sheath can be arranged in a position, and once the sheath 1200 is in the desired arrangement, a vacuum can be applied to the sheath, causing the walls of the sheath to press down against the rigid elements 1202. The pressure of the walls of sheath 1200 on the rigid elements 1202 causes them to press together and form a rigid mass, as shown in FIG. 12B. Once vacuum is released, the device can be re-shaped.

Figure 13A:
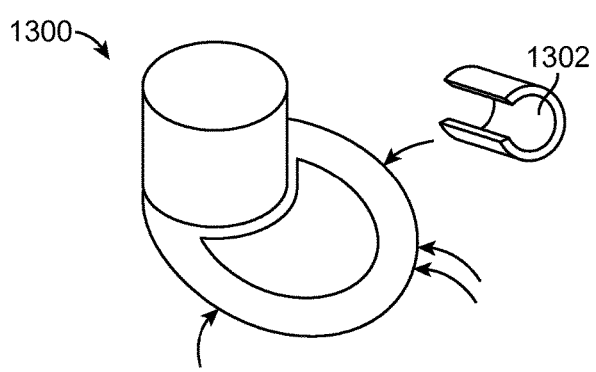
FIGS. 13A-B illustrate an embodiment of an adjustable intra-vaginal device.
Figure 13B:
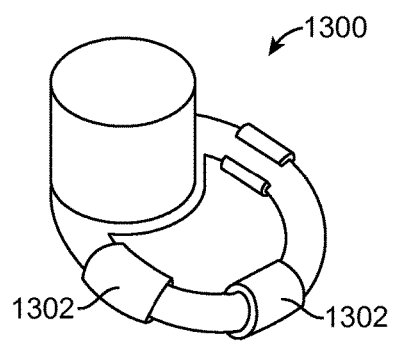

FIG. 13A illustrates an embodiment of a device 1300 onto which pieces of extra material 1302 can be positioned (e.g., snapped onto, interlocked with, adhered to). The extra material 1302 can use the contours of the device 1300 or other features such as snap fits, magnetic attachments and adhesives to retain its position on the device. The extra material 1302 can serve to add width, bulk, or surface area to a specific location of the device 1300. Pieces of extra material 1302 can be stacked or overlapped to create a more custom fit, as shown in FIG. 13B. Material 1302 can be soft or rigid. In the case of soft material, the softness can be used to provide extra padding to locations that can cause discomfort or injury to a patient due to the pressure the device exerts on the anatomy.

Figure 14A:
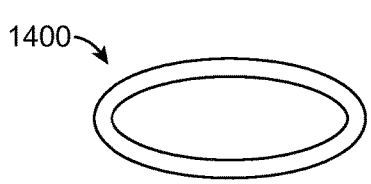
FIGS. 14A-C illustrate an embodiment of a device frame comprising a restraining mechanism to prevent adjustability of the device in certain configurations.
Figure 14B:
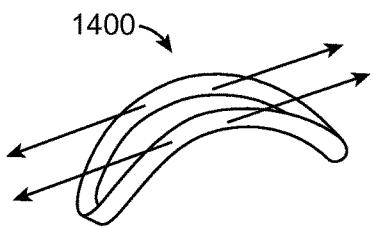
Figure 14C:
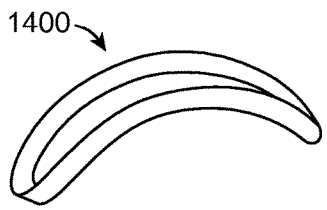

In some embodiments, to prevent unintentional adjustment, adjustability can be limited to occurring only while the device frame is partially folded and prevented when the device frame is fully relaxed or fully folded. This feature may prevent unintentional adjustment while the device is in place or during insertion. Such a feature can comprise internal sliding components with keyed features. FIG. 14A illustrates an embodiment of a device frame 1400 comprising an adjustment prevention feature. FIG. 14B shows the device frame 1400 partially folded, disengaging the key. With the keying disengaged, the device frame 1400 is free to be adjusted, as shown in FIG. 14C.

Figure 15A:
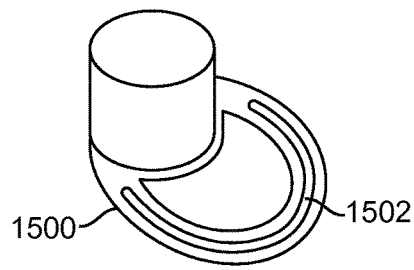
FIGS. 15A-D illustrate an embodiment of an adjustable intra-vaginal device.
Figure 15B:
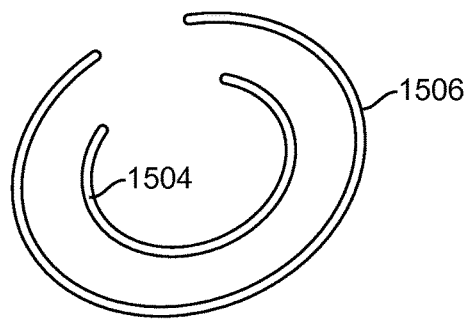
Figure 15C:
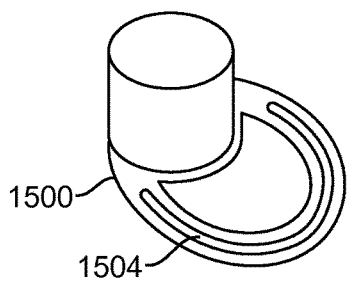
Figure 15D:
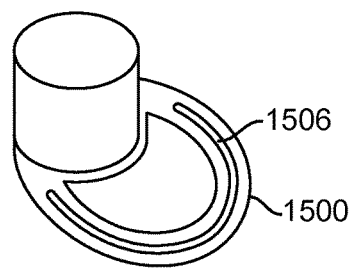

FIG. 15A illustrates a device with a flexible and stretchable base 1500 with a pocket 1502 that can accommodate different frame sizes. FIG. 15B illustrates embodiments of differently sized frame pieces 1504, 1506. FIG. 15C illustrates the device with frame piece 1504 inserted into the base 1500. FIG. 15D illustrates the larger device with frame piece 1506 inserted into the base 1500.

Figure 16A:
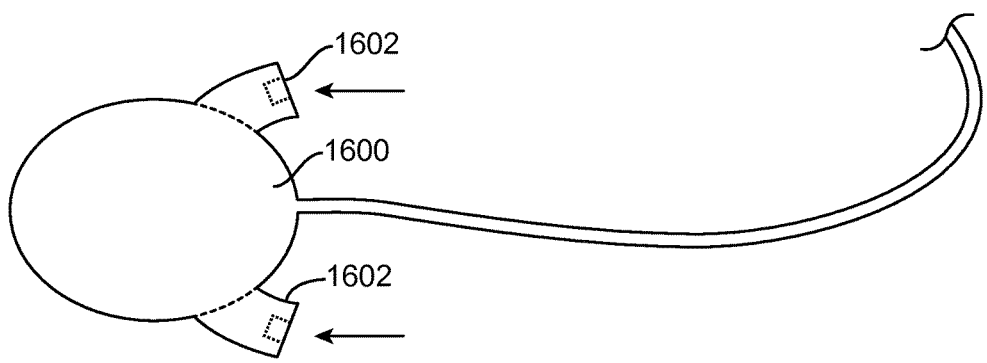
FIGS. 16A-B illustrate an embodiment of an adjustable intra-vaginal device.
Figure 16B:
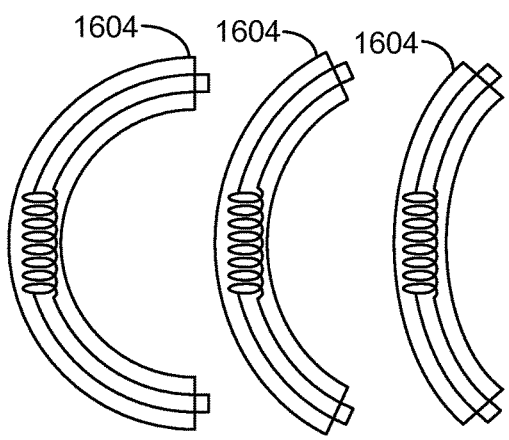

FIG. 16A illustrates an embodiment of a modular device. The device can have connectors 1602 on the expandable body portion 1600. Differently shaped or sized frame sections 1604, shown in FIG. 16B, can snap into the connectors 1602 to produce differently sized and/or shaped devices.

FIG. 17A illustrates a device frame 1700 comprising an internal shape memory element 1702. The shape memory element 1702 can be formed into a particular shape (e.g., a large shape) and then mechanically compressed or cooled to change the shape (e.g., reduce the size of the shape), as shown in FIG. 17B. Once in place, allowing the device to expand or come to body temperature can cause it to recover the original shape. In a particular embodiment, the shape memory element 1702 can be sized and shaped such that the vaginal walls provides sufficient resistance to prevent a complete recovery. In this way, the device can adapt to the vaginal anatomy of a given patient. In another embodiment, the more open configuration is the cooled stated of the coil, and a temporary increase in temperature above its transition temperature (AF point) via heat transfer or a passed current causes it to tighten up for insertion. An AF point greater than 37° C. but less than 60° C. would prevent the heated phase from being uncomfortable to the patient.

FIG. 18A illustrates an embodiment of a device frame comprising a solid band 1800, maintained in a coil. The band can be adjusted using a fixation mechanism 1802, such as a suture, clasp, or clamp which allows for the amount of overlap within the coil to be adjusted. FIG. 18B illustrates a detailed view of a clamp 1802 fixing overlapping sections in place. FIG. 18C illustrates an embodiment of a frame 1810 in which overlapping sections are configured to feed back into the frame. The overlapping section can enter an aperture 1812 in the frame 1810 comprising a seal 1814 around the tip of the frame 1810. The tip can be housed within a chamber that can be hydraulically or mechanically driven to change the frame size.

FIG. 19 illustrates an embodiment of a device frame 1900. The frame 1900 comprises curved segments 1902 with interlocking teeth 1904. When clamped, the teeth 1904 can stabilize the frame 1900 shape. As shown in FIG. 19, frame 1900 has hinges 1906, and can be folded for insertion and removal. As shown, segments 1902 can be curved. Straight segments may cause the resulting interlocked structure to be out-of-round as the overlapping portion of the segments can result in additional straightening spring force. This additional straightening force can be adjusted for by biasing the segments to be curved. When the segments are biased to be curved to form the overall smallest diameter or roundest shape, as the overall diameter is increased, spring forces of the curved segments can essentially balance each other out, resulting in a rounder overall shape. Different spring constants and segment curvatures can be used alone, or in combination, to achieve different desired overall frame shapes and stiffnesses.

Figure 20A:
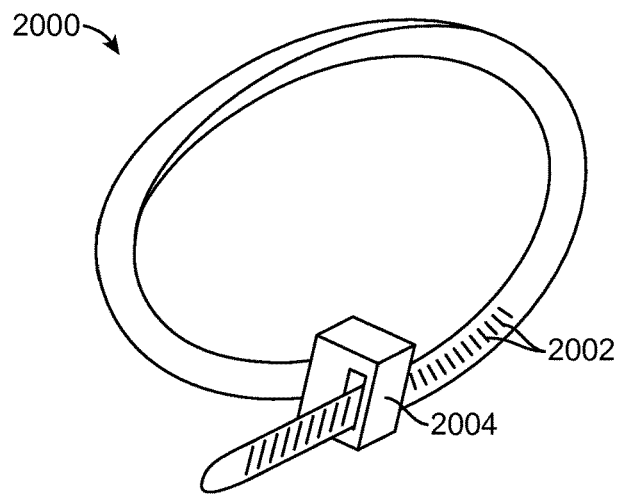
FIGS. 20A-B illustrate an embodiment of an adjustable intra-vaginal device.
Figure 20B:
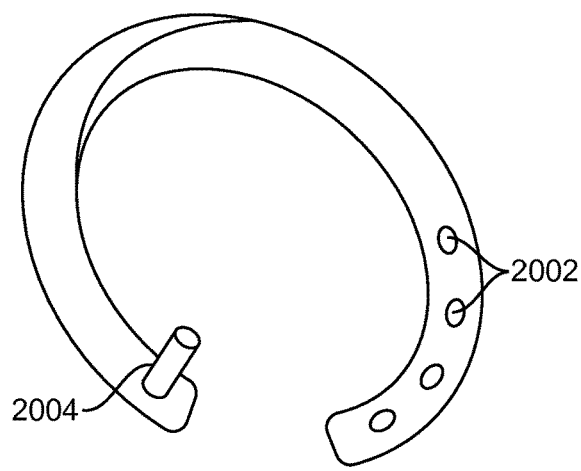

FIG. 20 illustrates an embodiment of a device frame 2000 comprising a band with multiple female or male features 2002 at one end that can mate with a male or female feature 2004 on the opposing end once a desired size is reached. In some embodiments, the adjustment is done via ratcheting features, for example, like a zip-tie, as shown in FIG. 20A. In other embodiments, the adjustment is done discretely, like a belt buckle, as shown in FIG. 20B.

Figure 21:
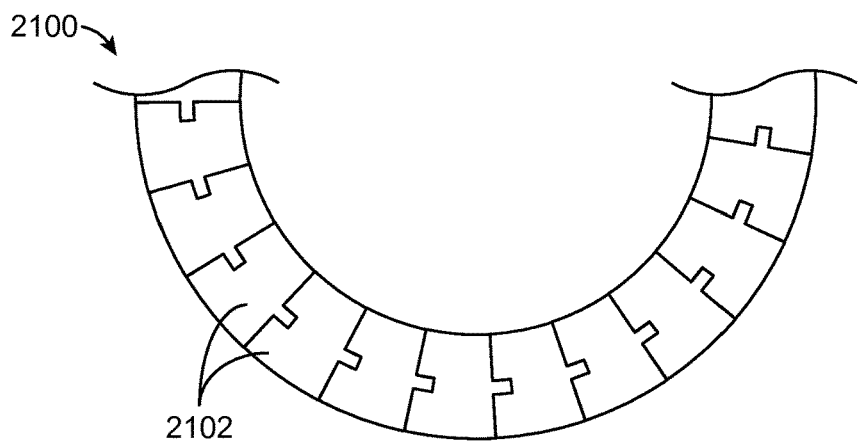
FIG. 21 illustrates an embodiment of an adjustable intra-vaginal device.

FIG. 21 illustrates an embodiment of a device frame 2100 comprising multiple interlocking pieces 2102. The size of the frame 2100 can be adjusted by adding or removing an appropriate number of pieces 2102.

Adjustable devices as disclosed herein may be permanently locked before insertion in a patient using secondary tools (e.g., rivets), welding, heat sealing, other mechanical means, and the like.

Adjustability performed in-situ can also help facilitate insertion and removal of the device by reducing the size of the device. It will be appreciated that adjustability can be provided in conjunction with the collapsing mechanisms provided in PCT Application No. PCT/US2014/016549, filed on Feb. 14, 2014, entitled "INTRA-VAGINAL DEVICES AND METHODS FOR TREATING FECAL INCONTINENCE" and U.S. application Ser. No. 14/181, 576, filed on Feb. 14, 2014, entitled "INTRA-VAGINAL DEVICES AND METHODS FOR TREATING FECAL INCONTINENCE".

In some embodiments, adjustability can be achieved using straight components configured to move relative to one another in a linear fashion. Such embodiments can incorporate a locking mechanism or use additional components to limit or allow relative movement between the straight components so that the straight components can have different amounts of overlap of segments comprising the straight components. A variety of locking mechanisms can be used, including mechanisms that are depressed, pulled or twisted to release the lock. In some embodiments, locking mechanisms move with adjustable components. In other embodiments, locking mechanisms are static relative to surrounding components.

Figure 22:
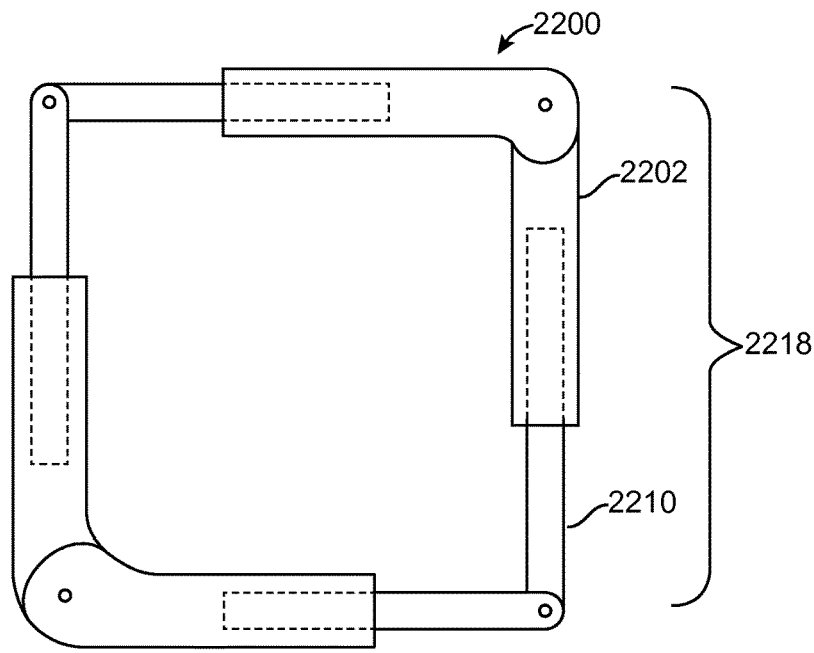
FIG. 22 illustrates an embodiment of an adjustable device frame.
Figures 23A, 23B:
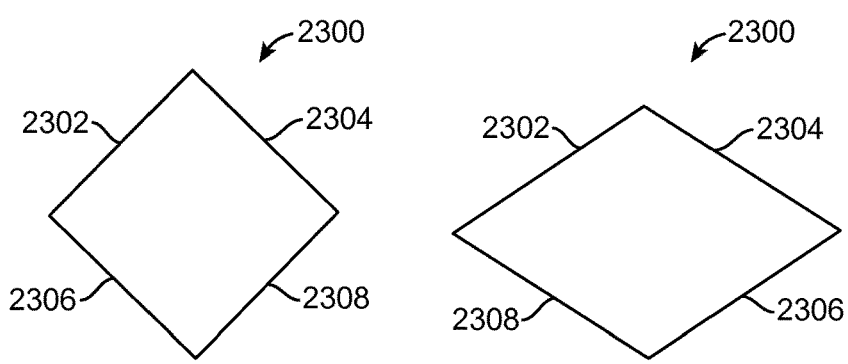
FIGS. 23A-23D illustrates an embodiment of an adjustable device frame in various configurations.
Figures 23C, 23D:
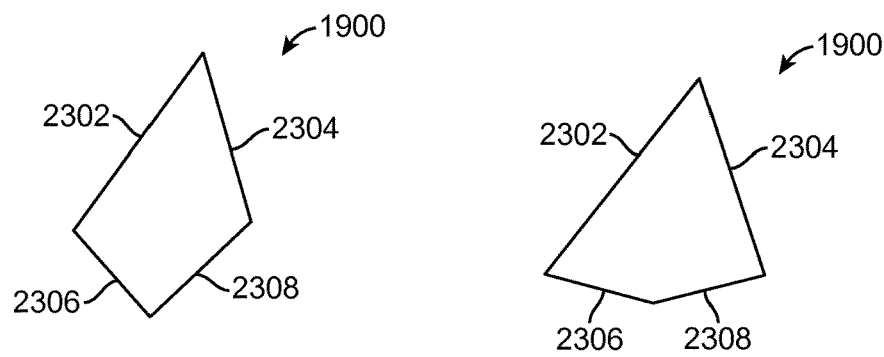

FIG. 22 illustrates an embodiment of a device with a frame 2200 consisting of 4 arms, connected at joints, wherein the arms can be extended. Each arm (e.g. 2218) comprises two segments that overlap (e.g. 2202, 2210). The arms are extended by changing the amount of overlap in their segments. By extending the arms (individually or in combination), the distance between joints increases and different sized frames are realized. The arms can be locked at various lengths by fixing the amount of overlap in the segments (e.g. by fixing the segments to each other). This frame can be surrounded by a flexible material (e.g. silicone, polyurethane) that stretches or shrinks to accommodate the different sized frames. The frame can be collapsed to allow insertion and removal of the device by the arms rotating with respect to each other at hinges. One or more of the hinges can be locked to secure the frame in an open position. In some embodiments, one or more of the hinges is configured to be able to lock at several different angles. In this way the length and width ratio of the device can be changed without changing the individual arm lengths. For example, FIGS. 23A-D illustrate 4 versions of a 4-arm configuration as described above with a lockable hinge 2300. In all 4 versions, arms 2302, 2304, 2306, 2308 are able to be lengthened or shortened as described above. Additionally, hinge 2300 can be locked at various angles. As a result many different configurations of arm lengths and length-width ratios are possible.

Figure 24A:
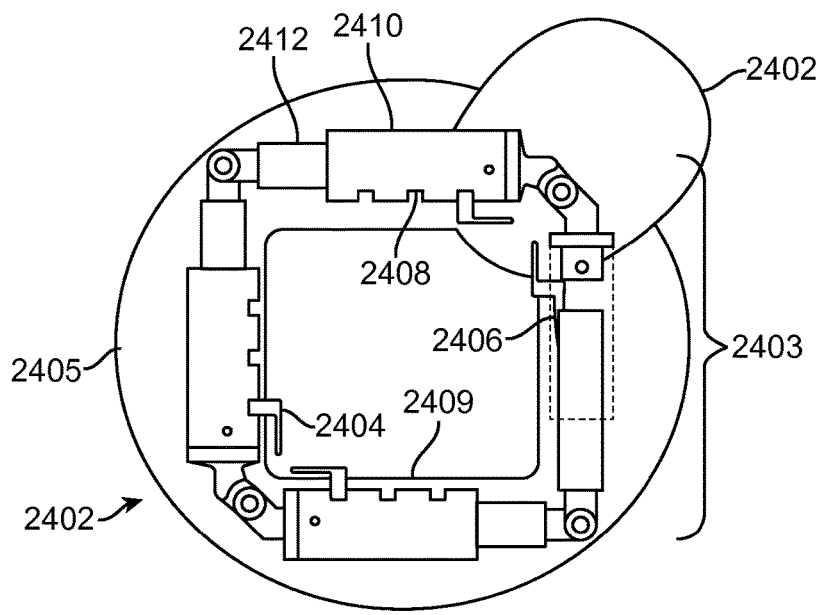
FIGS. 24A-B illustrate an embodiment of an adjustable intra-vaginal device frame.
Figure 24B:
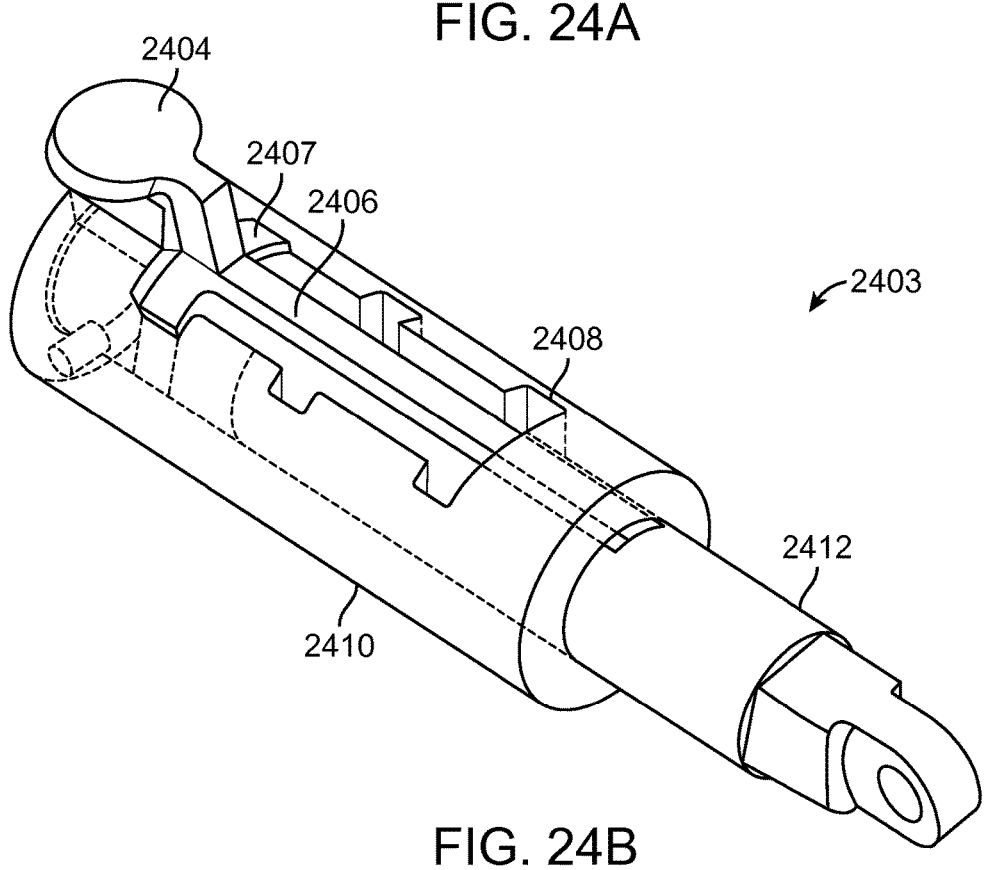

FIGS. 24A and 24B illustrate an embodiment of a device 2400 with frame 2401 comprising arms (e.g. 2403) that comprise inner segments (e.g. 2412) and outer segments (e.g. 2410) that are slidingly engaged. The amount of overlap between segments (e.g. segments 2412 and 2410) can be adjusted by sliding said segments with respect to each other. FIG. 24B shows a close-up view of one arm (e.g. 2403). Inner segment 2412 comprises a lever 2406 which terminates at one end with a button 2404. Proximate and attached to the button is a locking feature 2407. This locking feature 2407 fits into cut-outs 2408 on the outer segment 2410. With the locking feature 2407 engaged in the cut-out 2408, the inner and outer segments 2412,2410) are secured and cannot slide with respect to each other. When button 2404 is depressed, locking feature 2407 drops below cut-out 2408 and into the hollow center of outer segment 2410. Inner segment 2412 and outer segment 2410 are then able to slide with respect to each other. In this way, each arm of frame 2401 can be adjusted to discrete lengths to adjust the overall size of device. Exterior covering material 2405 is also shown covering frame 2401, creating a rounder profile than the frame alone. Exterior covering material 2405 leaves an opening in the center of the frame 2401 defined by edge 2409 of the covering. Occluding portion 2402 is also shown approximately over one joint of frame 2001.

Figure 25A:
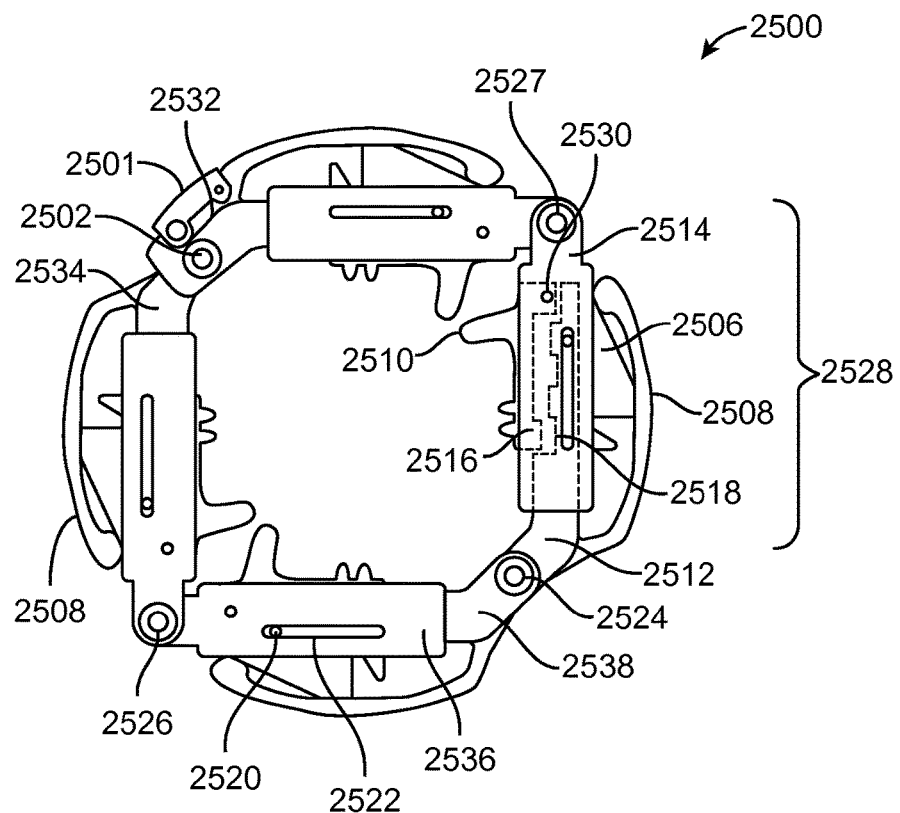
FIGS. 25A-D illustrate an embodiment of an adjustable intra-vaginal device frame.
Figure 25B:
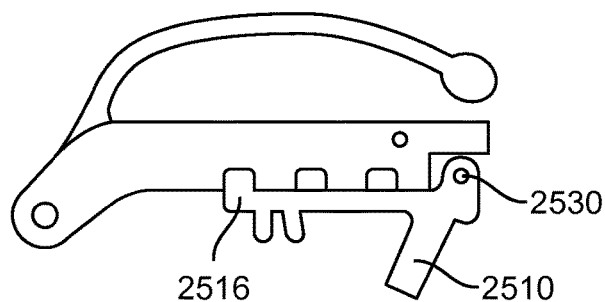

FIG. 25A illustrates an embodiment of a device with frame 2500 with linearly-extendable arms. An exemplary arm 2528 comprises an inner segment 2512 that slides within an outer segment 2514. Outer segment 2514 includes a hinged lever 2510 that comprises a tooth 2516, shown in more detail in FIG. 25B. This tooth 2516 can fit into pockets (e.g. pocket 2518) along the length of inner segment 2512. When tooth 2516 is engaged with a pocket (e.g. pocket 2518) on inner segment 2512, the segments 2512, 2514 are not allowed to slide relative to each other, and arm 2528 length is fixed. Lever 2510 rotates about hinge 2530. When lever 2510 is rotated clockwise about hinge 2530, tooth 2516 lifts out of pocket 2518, allowing the segments 2512,2514) to slide relative to each other to change the length of arm 2528. A spring or elastomeric element can be used to cause lever 2510 to return into a locked position.

Figure 25C:
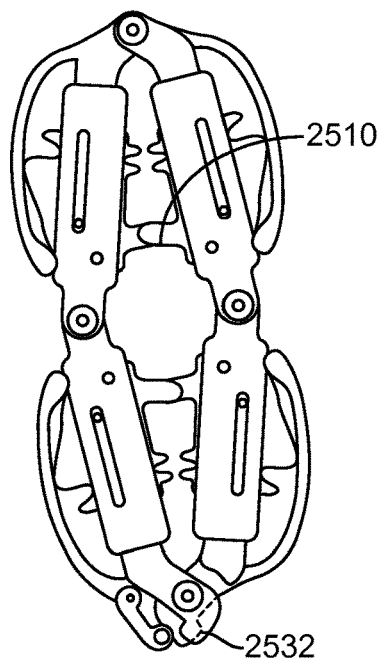

Latch 2501 at hinge 2502 can lock the arms, preventing frame 2500 from collapsing. FIG. 25C shows this embodiment in collapsed state. The ability to adjust the frame 2500 to be in a collapsed or collapsible state can be useful during inserting and/or removal of an intra-vaginal device. Latch 2501 of FIG. 25A prevents rotation of hinge 2502 by preventing rotation of segment 2534 about hinge 2502. This is accomplished by latch 2501 interfering with the path that tooth 2532 (a portion of segment 2534) makes as it rotates around hinge 2502. When latch 2501 is lifted, tooth 2532 is allowed to move, and the whole device can collapse.

FIG. 25A also illustrates a constraint to prevent over-lengthening of segments (e.g. segments 2512, 2514). Outer segment 2536 (for example) contains a slot 2522, cut through its wall. Pin 2520 is fixed to inner segment 2538. When inner segment 2538 is slid out of outer segment 2536, pin 2520 will reach the extent of slot 2522 and allow no further lengthening.

Figure 26A:
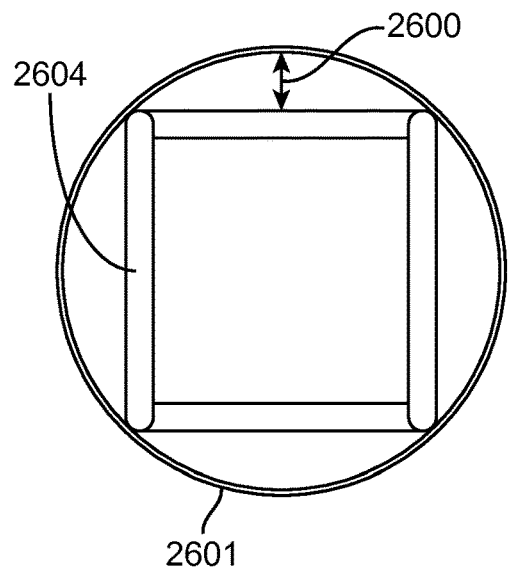
FIGS. 26A-B illustrate an embodiment of an adjustable intra-vaginal device frame.
Figure 26B:
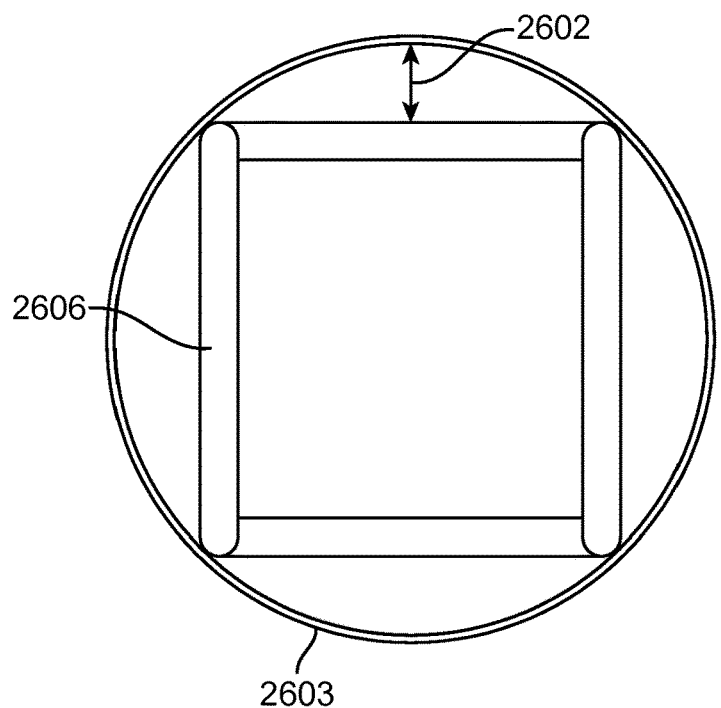
Figure 27A:
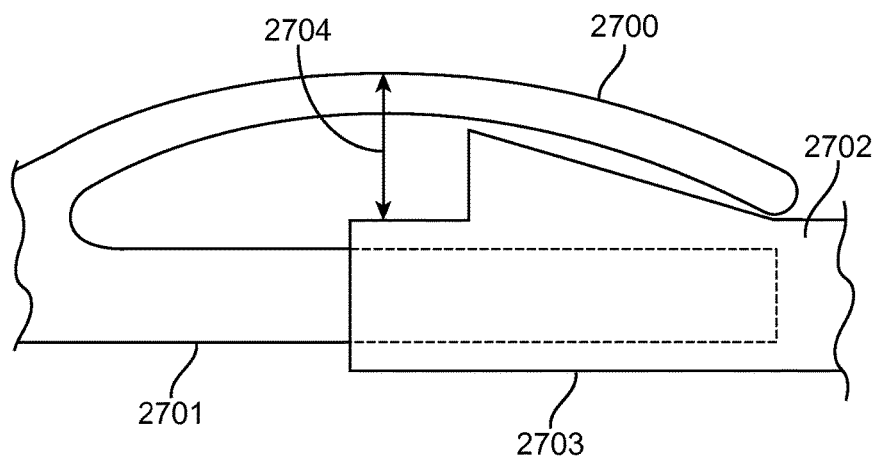
FIGS. 27A-B illustrate an embodiment of a rounding feature of an adjustable intra-vaginal device frame.
Figure 27B:
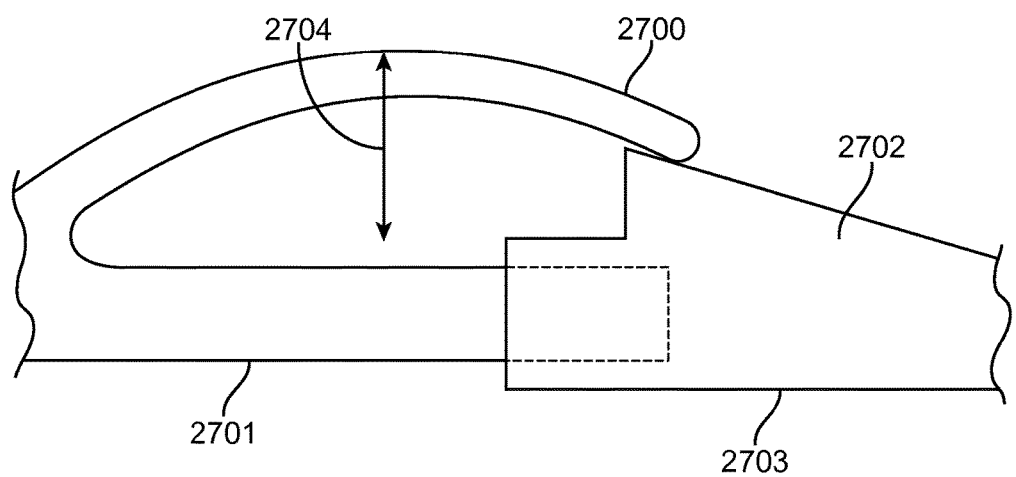

FIG. 25A illustrates a feature 2508 that creates a rounded outer profile for the device. A rounded outer profile can allow the device to best distribute forces to the vaginal walls and minimize potential for injury or discomfort. While a rounded outer profile can be created by a covering material, such as silicone, or a fixed solid rounded feature, there can be limitations in how well such a feature approximates a curve as the arms of the frame are expanded. Illustrating this is FIGS. 26A and 26B. In FIG. 26A, diamond 2604 is inscribed in circle 2601. There is a gap between the edge of circle 2601 and diamond 2604 noted by arrow 2600. FIG. 26B shows a larger diamond 2606, with a corresponding circle 2603 in which it is inscribed. Gap 2602 is larger in FIG. 26B than gap 2600 of FIG. 26A. As shown in FIGS. 26A and B, a device utilizing an angular frame, such as a diamond-shaped frame with a static feature to approximate a round contour will become less round as its frame expands to larger sizes. The embodiment of FIG. 25A addresses this issue via its use of flexible arches. The embodiment of FIG. 25A uses arches (e.g. arch 2508) to provide a more rounded outer profile. Arch 2508 is attached to inner segment 2512. As inner segment 2512 is slid out from outer segment 2514, arch 2508 slides up ramp 2506 (which is part of outer segment 2514). As arch 2508 slides up ramp 2506, the ramp 2506 causes the arch 2508 to extend farther away from the segments. This allows the device to provide a smoother, rounder outer profile. FIGS. 27A and 27B show a close-up of similar arch 2700 that slides up ramp 2702 as inner segment 2701 is slid out from outer segment 2703. Distance 2704 is greater in FIG. 27B than in FIG. 27A.

Figure 25D:
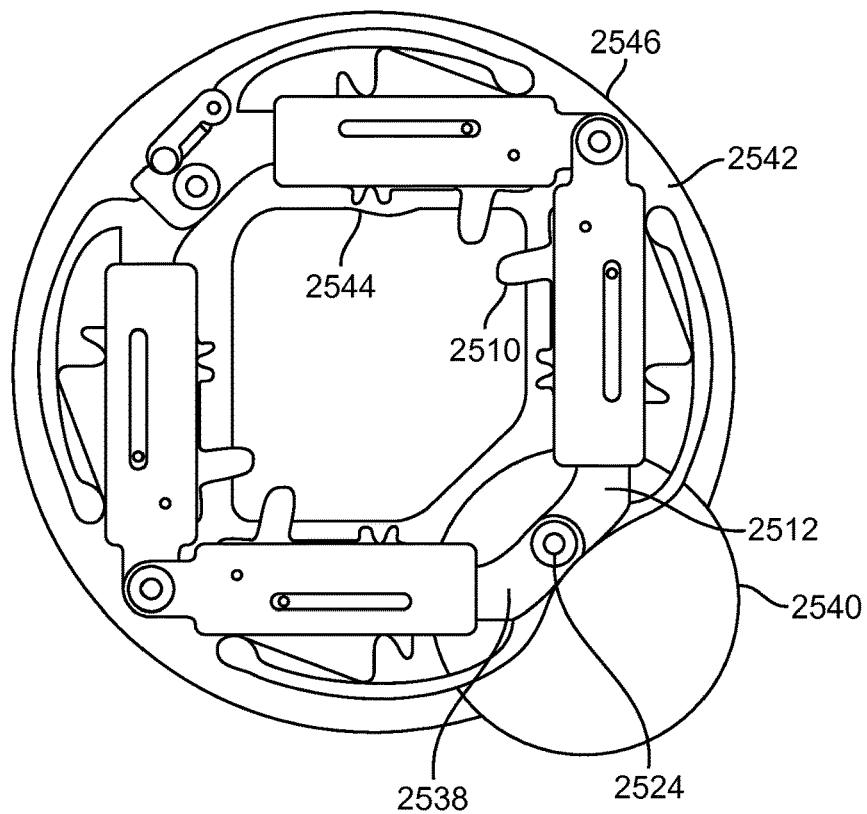

FIG. 25D illustrates the frame of 25A inside of an exterior covering 2542. This exterior covering can be made of a soft material (e.g. silicone, polyurethane) and is at least partially elastomeric so it can stretch to accommodate the expansion of the frame. The exterior cover 2542 has an outer profile 2546, and can comprise an annulus, shown here with an inner perimeter 2544. Levers (e.g. lever 2510) are operable through the inner perimeter of the exterior covering 2542. Levers (e.g. lever 2510) can be covered with a thin layer of material that can be contiguous with the exterior covering 2542. Also illustrated in FIG. 25D is an occluding portion 2540, shown approximately over hinge 2524. This occluding portion 2540 is connected to the outer covering 2542. The outer covering 2542 is, in some embodiments, not connected to the portion of the frame in proximity to the occluding portion 2540 allowing the occluding portion 2540 to float over hinge 2524 and therefore be less affected by lengthening of segments and collapsing of the frame. Occluding portion 2540 can also be attached to the frame, in which case the occluding portion can be attached to the frame such that it will not be stretched when the frame is expanded. For example, occluding portion 2540 can be attached to the portions of inner segments 2512, 2538 that are not overlapping outer segments 2514, 2536, respectively, so that when inner segments 2512, 21438 are slid out from their respective outer segments, the occluding portion remains in the same position.

The device of FIGS. 25A-25D has two offset hinges, 2524 and 2502. Whereas hinges 2526 and 2527 are at the approximate intersection of the centerlines of adjacent arms, hinges 2524 and 2502 are biased more towards the center of the assembly. This offset allows for more space between components when the device is collapsed as shown in FIG. 25C. The additional space is beneficial to accommodate mechanisms used to adjust the size of the device (e.g. lever 2510) and to accommodate the folding of the exterior covering material at the joints. Levers (e.g. lever 2510) are also offset in height so that they do not collide during collapse. The shape and offset at hinge 2524 also accommodates more space for the occluding portion 2540 (FIG. 25D) and any supporting structures for the occluding portion. Additionally, in some embodiments, the device includes additional soft material around the occluding portion and the stabilizing body proximate to the occluding portion, as described in for example, U.S. Publication No. 2013/0138135 (application Ser. No. 13/679,484), filed Nov. 16, 2012, entitled "INTRA-VAGINAL DEVICES AND METHODS FOR TREATING FECAL INCONTINENCE"; U.S. Publication No. 2013/0144112 (application Ser. No. 13/679,528), filed on Nov. 16, 2012, entitled "INTRA-VAGINAL DEVICES AND METHODS FOR TREATING FECAL INCONTINENCE"; the offset and shape of hinge 2524 allows for more soft material between it and the outer perimeter 2546 of the exterior coating 2542.

The segments that comprise the arms of frame 2500 have rectangular cross-sectional profiles. This shape can help ensure uniform alignment between slidingly engaged segments and prevents rotation between slidingly engaged segments. Pin-and-slot features such as slot 2522 and pin 2520 also help ensure alignment and prevent rotation. Alignment and lack of rotation within arms can help to maintain a planar configuration. If, for example, all four arms consisted of inner and outer segments with round cross-sections and no alignment features, such that the segments forming the arms could rotate with respect to each other, the frame would allow out-of-plane motion.

Figure 28:
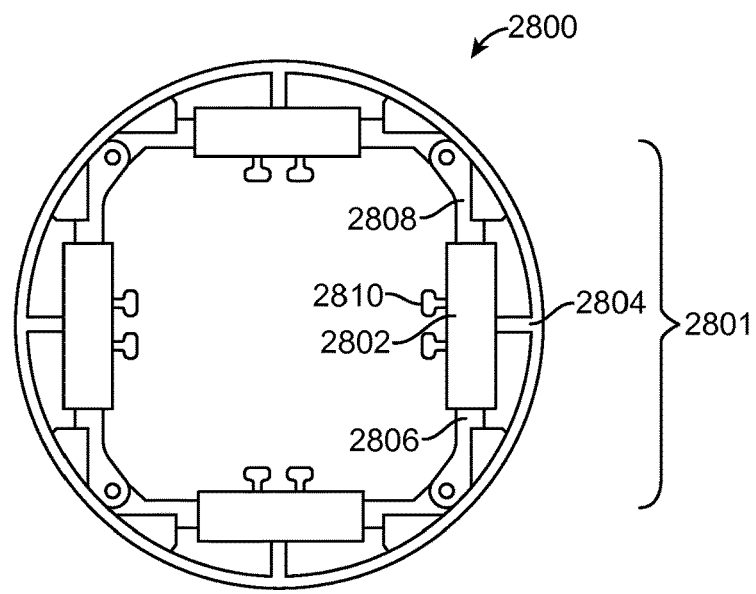
FIG. 28 illustrates an embodiment of an adjustable intra-vaginal device frame.

FIG. 28 illustrates an embodiment of a device comprising a frame 2800. In this embodiment, arm 2801 comprises 3 segments: 2 inner segments 2808 and 2806, and 1 outer segment 2802. Buttons (e.g. button 2810) can be pushed to allow inner segments (e.g. inner segment 2808) to slide with respect to its outer segment 2802. The more centrally-located buttons (e.g. button 2810) can be easier to manipulate than mechanisms closer to the corners as they are free from the tight corners of the frame. Frame 2800 also has an arch 2804 to approximate a round shape in at least one size.

Figure 29A:
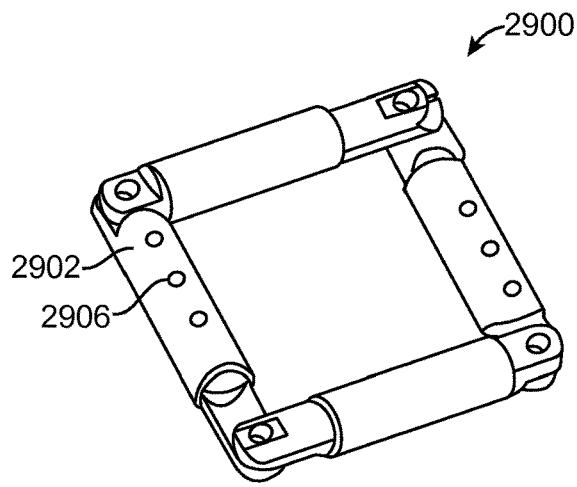
FIGS. 29A-B illustrate an embodiment of an adjustable intra-vaginal device frame.
Figure 29B:
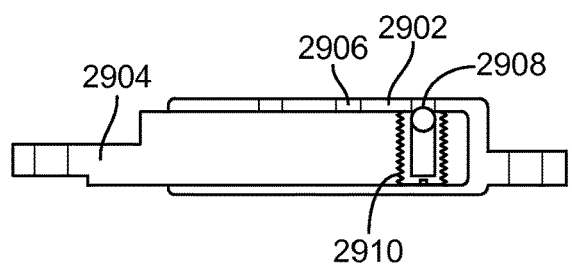

FIG. 29 illustrates an embodiment of a device comprising a frame 2900. Frame 2900 can expand similar to the example of FIG. 25A, consisting of 4 arms, joined by hinges. The arms of frame 2900 comprise segments with round cross-sections (e.g., inner segment 2904 and outer segment 2902). To adjust the overlap between these segments, inner segment 2904) can be slid with respect to outer segment 2902. A detent mechanism is used to secure the segments at a given amount of overlap. As the inner segment 2904 is slid within outer segment 2902, inner segment 2904 reaches a point where a feature on inner segment 2904 engages a hole 2906 on outer segment 2902 and the segments are secured until sufficient force is applied to overcome the engagement. FIG. 29B shows a cross section of the inner and outer segments 2904, 2902. A threaded ball detent mechanism comprising ball 2908 and housing 2910, is shown at part of the inner segment 2904. Ball 2908 is configured to engages the holes (e.g. hole 2906) of the outer segment 2902.

Figure 30:
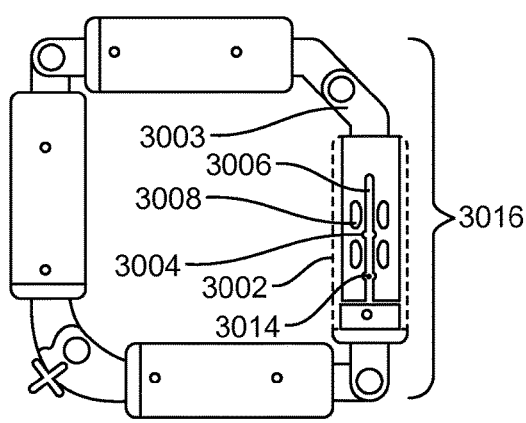
FIG. 30 illustrates an embodiment of an adjustable intra-vaginal device frame.

FIG. 30 illustrates an embodiment of frame 3000, comprising arms that utilize segments comprising a round-cross section, and uses a pin-detent mechanism to stabilize the lengths of its overlapping arms (e.g. arm 3016). In this embodiment, inner segment 3003 has a groove 3006 with wider portions 3004. A pin 3014 is connected to outer segment 3002 and spans its inner diameter and is configured to fit snugly in the wider portions 3004 in slot 3006. When the inner segment 3003 is slid with respect to outer segment 3002, the pin passes through the narrower portions of slot 3006 that are between the wider portions 3004. Flexure pockets 3008 are provided to allow deflection of the walls of slot 3006 as pin 3014 passes through the narrow portions. The segments and components within are configured such that greater force is required to transition the segments from a position where pin 3014 is engaged in a hole (e.g. hole 3004) to a position where pin 3014 is between holes. In this way, discreet amounts of overlap can be secured with the slidingly engaged segments. Pin 3014 and slot 3006 also keep segments 3003 and 3002 aligned and prevent rotation.

Figure 31:
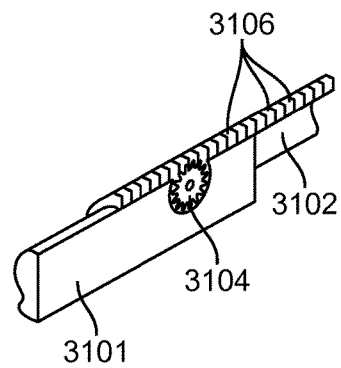
FIG. 31 illustrates an embodiment of an arm of an adjustable intra-vaginal device frame.

FIG. 31 illustrates an inner segment 3101 and an outer segment 3102, both in cross-section to show the internal mechanisms. These segments can form the adjustable arms in a configuration similar to those presented in FIGS. 30, 29, 25. In this embodiment, outer segment 3102 is configured to have gear teeth 3106 extending at least partially along its length. Inner segment 3104 includes a gear coupled to inner segment 3101. When gear 3104 is rotated, it moves outer segment 3102 over inner segment 3101, changing the amount of overlap between segments. Gear 3104 can be actuated by a member that extends outwards from the center of gear 3104, passing through a slot in the outer segment 3102 to enable access to the user.

Figure 32:
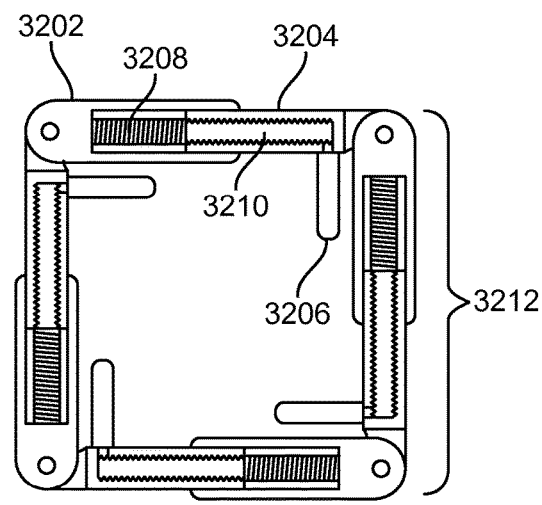
FIG. 32 illustrates an embodiment of an adjustable intra-vaginal device frame.

FIG. 32 illustrates a frame 3200, comprising four lengthening arms (e.g. arm 3212). Inner segments (e.g. inner segment 3204) have an internal hollow compartment 3210 that is fluidly connected to a port 3206. Outer segments (e.g. outer segment 3202) slidingly accept inner segments (e.g. inner segment 3204) and also contain an elongate member 3208 that slides within inner chamber 3210, forming a seal with the inner walls of chamber 3210. When fluid is introduced into chamber 3210, fluid pressure causes the elongate member 3208, and therefore the outer segment 3202 to move with respect to the inner segment 3204. Positive pressure pushes the segments apart. Negative pressure draws the segments together. Segments 3202 and 3204 should be configured as described in above embodiments to prevent rotation about each other and to provide alignment between each other. The fluid ports 3206 can be individually fluidly connected to a reservoir, or connected via a manifold or other means common in the art. An advantage of this embodiment is that it can be placed inside the vagina, and be adjustment of the frame size can be made via fluid pressures from outside of the body.

While many of the above embodiments comprised 4 individually adjustable arms, it is recognized that one skilled in the art can apply the features and concepts to any number of arms. Additionally, the scope of the invention is not limited to the specific mechanisms described for adjusting and securing the amount of overlap in the segments.

A variety of joint-locking features can be used to lock the joints connecting adjacent arms to secure the frames described in the embodiments above into open and/or collapsed states. A number of these joint-locking mechanisms are described in PCT Application No. PCT/US2014/016549, filed on Feb. 14, 2014, entitled "INTRA-VAGINAL DEVICES AND METHODS FOR TREATING FECAL INCONTINENCE" and U.S. application Ser. No. 14/181,576, filed on Feb. 14, 2014, entitled "INTRA-VAGINAL DEVICES AND METHODS FOR TREATING FECAL INCONTINENCE".

Disclosed herein are devices with a plurality of segments forming a frame, wherein one or more of the segments are adjustable lengthwise, and by adjusting the lengths of the segment or segments, the size and shape of the frame is changed. The stabilizing body used to secure the position of the occluding portion in the correct location can comprise the frames described herein. The length and width of the stabilizing body can be changed independently or together. In particular embodiments, the occluding body can be fixed on a portion of the stabilizing body that is at least partially decoupled from the adjustability of the frame.

In particular embodiments, the stabilizing body can be collapsible to facilitate easier insertion and removal. Designs such as those described above that utilize separate adjustable features that are interconnected by joints allowing relative motion (e.g. hinges or elastomeric connections) provide for both collapsibility and adjustability, therefore offering dual advantages. Moreover, when the joints joining the adjustable segments are configurable to different degrees of collapse or opening of the frame, a wide variety of shapes and sizes are possible (as demonstrated in FIGS. 23A-D). With these designs, the ability to place an occluding portion in the proper anatomical position of a patient with FI is enhanced.

In particular embodiments, there is an advantage to maintaining a rounded exterior profile. This is important for evenly distributing forces inside the vagina. Described herein are means for creating a rounded profile when linear segments comprise the stabilizing body. Means are also disclosed for maintaining the rounded exterior profile when the device is adjusted to a variety of different shapes and sizes.

While some of the embodiments described above utilize linear segments with adjustable amounts of overlap, the invention is not limited to linear segments. Curved, or flexible segments can be used as well, preferably with means of changing and securing the amount of overlap between curved segments. In some embodiments these curved segments are joined by joints that allow relative motion to facilitate collapse of the device, or to facilitate a wider range of length-width ratios.

A general concept disclosed herein includes a plurality of arms comprising the stabilizing body for support of an occluding portion. At least one of the arms is configured to be adjustable. The arms are joined by joints that allow relative motion (e.g., angular) between adjacent arms. At least one of these joints can be locked to constrain or limit motion at that joint, having the effect of fixing the stabilizing body in one or more open configurations, and/or in a closed configuration. As an alternate to the locking joint, spring forces can be used to resist relative motion between adjacent arms.

The advantage of the general concept described above is enhanced ability to stabilize the occluding portion in the correct position in a patient's anatomy.

In some embodiments, adjustable frames incorporate passive mechanisms to lock relative motion between adjustable components. For example, friction balance, magnetic interaction, flexure features, or ball detents may be used. In some embodiments, adjustability may be provided in discrete adjustments. In some embodiments, adjustability may be provided in continuous adjustment.

The above mentioned adjustable inventions are not limited to devices for the treatment of fecal incontinence, but could potentially be used for beneficial improvements of vaginal devices in general, including pessaries for pelvic organ prolapse, pessaries for urinary incontinence, vaginal devices for contraception, vaginal devices for management of menstrual fluids, vaginal devices for post-surgical bleeding control, or vaginal devices for the delivery of pharmaceuticals.

Figure 33:
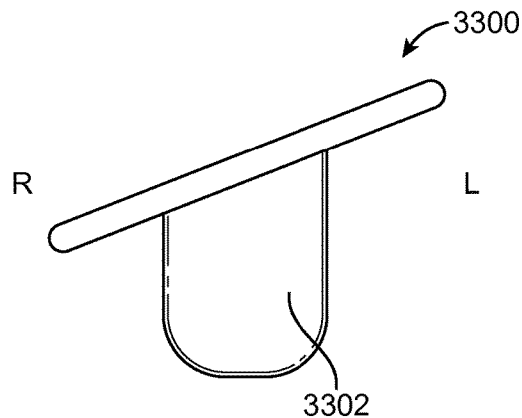
FIG. 33 illustrates an embodiment of an intra-vaginal device configured to accommodate particular patient anatomy.

In some embodiments, the device tilts to one side due to an anatomical feature of a particular patient. FIG. 33 illustrates an embodiment of a device 3300 configured to anticipate such a tilt and allow the expandable body 3302 to depress the rectum centrally. The expandable body is not uniformly shaped, and is longer on the side of the device that is tilting away from the expandable body. The increased length of one side of the expandable body can accommodate for the tilt of the device. In some embodiments, a device can accommodate for tilting using plastic deformation or a friction fitting.

Inflatable Devices

In some embodiments, it may be advantageous to have a largely or completely inflatable device. For example, an inflatable device can help facilitate insertion and removal as large portions of the device can be deflated during insertion and removal. The deflation can decrease the size and cross-sectional profile of the device by 4 fold or more. Deflation can also reduce rigidity of the device, allowing it to more easily be inserted or removed from the vagina with its curves and folds, as well as allowing it to be formed into a curved or other shape to facilitate insertion In the prior art, the deformable device required the user to counter the spring opening force while orienting and inserting it. An inflatable device that utilizes air pressure to stabilize itself in the vagina, when deflated, would not present any active opening forces for the user to counter. Additionally, inflation of the device can be controlled, providing comfort to the user. Inflation can be used to control both device size and stiffness. Inflation can be reduced during times of increased sensitivity. It can then be gradually increased as the user becomes more comfortable, providing better stabilization or occlusion. An inflatable device can also provide cushioned surfaces, also providing comfort to the user. Cushioned surfaces better distribute the force of the device on the tissue and can better react to dynamic changes, reducing tissue damage and damage to the device. Inflatable design can be applied to other intra-vaginal devices, for example, pessaries. An inflatable stabilizing portion can allow better conformance to a larger variety of patient anatomies than rigid alternatives. This form can be compressed into longer or wider shapes starting from the same initial footprint. In yet other embodiments, inflatable portions are in addition to the stabilizing portion, or constitute combinations of the stabilizing, extendable, or other portions.

Figure 34A:
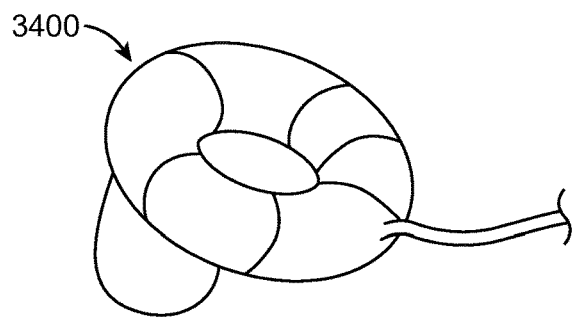
FIGS. 34A-B illustrate an embodiment of an inflatable intra-vaginal device.
Figure 34B:
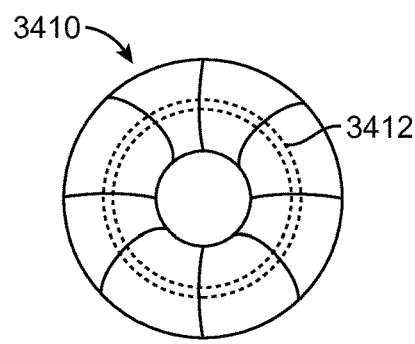

FIG. 34A illustrates an embodiment of a device 3400 comprising an inflatable toroidal stabilizing body. The inflatable body allows for a larger effective surface area than would a rigid frame with the same cross-sectional area as measured in its insertion/removal state. In its inflated state, the toroidal shape has a high ratio of surface area to thickness, $4\pi 2R$, where R is the diameter of the stabilizing body. Increasing surface area, but not height, can prevent the redundant tissue of the vagina from being stretched, preserving occlusion efficacy and allowing the vaginal tissue to more fully intrudes upon the stabilizing body interior, increasing stability and reducing localized pressures. FIG. 34B illustrates an embodiment of a device 3410 comprising a structure 3422 inside the device. The structure 3412 is configured to help orient and provide structure to the device during insertion. The structure 3412 can also be positioned alongside the device 3410. The structure 3412 can be a flexible band. In some embodiments, the structure 3412 comprises collapsing or locking mechanisms as described in PCT Application No. PCT/US2014/016549, filed on Feb. 14, 2014, entitled "INTRA-VAGINAL DEVICES AND METHODS FOR TREATING FECAL INCONTINENCE" and U.S. application Ser. No. 14/181,576 filed on Feb. 14, 2014, entitled "INTRA-VAGINAL DEVICES AND METHODS FOR TREATING FECAL INCONTINENCE".

Figure 35A:
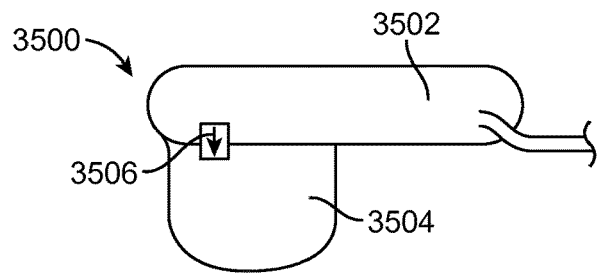
FIGS. 35A-C illustrate an embodiment of an inflatable intra-vaginal device.
Figure 35B:
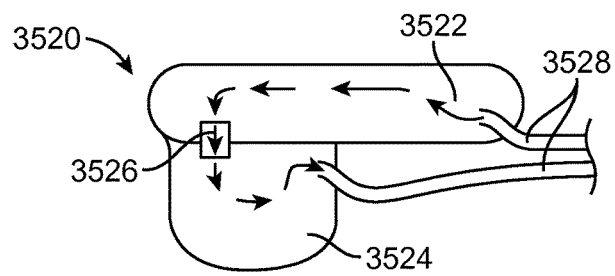
Figure 35C:
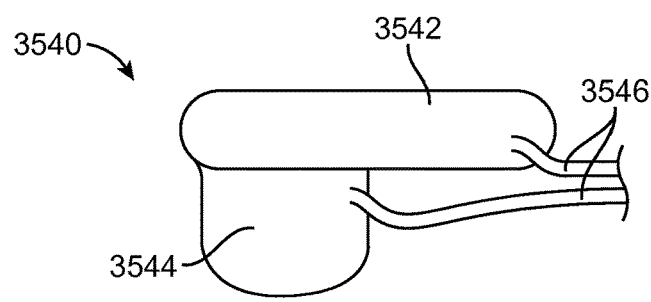

In some embodiments, an inflatable device can have multiple chambers. FIG. 35A illustrates an embodiment of a device 3500 comprising an inflatable chamber 3502 in the stabilizing body and an inflatable chamber 3504 in the expandable body. A pressure relief valve 3506 can control air or fluid flow from the stabilizing body chamber 3502 to the expandable body chamber 3504. The valve 3506 can establish a pressure drop so that the expandable body chamber 3504 is set to a lower pressure than the stabilizing body chamber 3502, allowing the stabilizing body chamber 3502 to be stiffer. In some embodiments, the expandable body chamber 3504 can be inflated first, reversing the relative pressure of the chambers. FIG. 35B illustrates an embodiment of a device 3520 comprising a stabilizing body chamber 3522 and an expandable body chamber 3524, with a pressure relief valve 3526 between them. The device 3520 allows air or fluid to be removed from either chamber through lumens 3528. This ability can allow further control over pressure of the device 3520. FIG. 35C illustrates an embodiment of a device 3540 comprising a stabilizing body chamber 3542 and an expandable body chamber 3544 that do not communicate and are controlled by separate inflation tubes 3546.

Figure 36A:
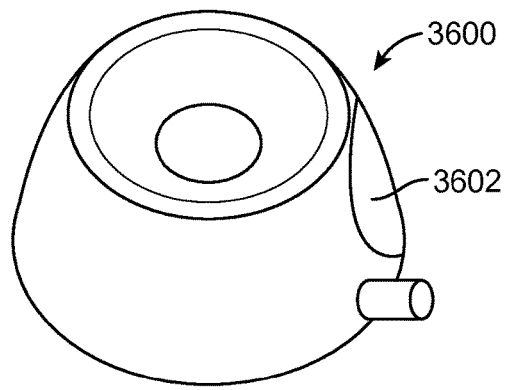
FIGS. 36A-36B illustrate an embodiment of an inflatable stabilizing body.
Figure 36B:
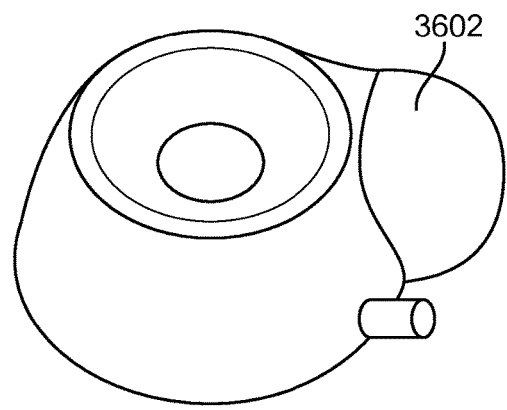

In some embodiments, portions of the device (e.g., stabilizing body, expandable body) are configured to expand different amounts during inflation. Allowing portions of the device to expand different amounts can create unique device shapes. FIG. 36A illustrates an embodiment of a stabilizing body 3600 comprising a portion 3602 configured to expand more at a given pressure than other portions of the stabilizing body. Portion 3602 comprises thinner walls than other portions of the stabilizing body, causing it to expand more, as shown in FIG. 36B. Such section can be used to engage specific tissues to increase stability or to target less sensitive, more robust tissues. In other embodiments, expansion can be controlled by wall features such as corrugation, reinforcement with tensile elements, or by filler materials like open cell foams.

Sizing Tools

Intra-vaginal devices disclosed herein may be provided in multiple sizes and/or shapes. In some embodiments, adjustable intra-vaginal devices are provided. In both cases, a particular device, size, or shape must be selected for particular patient anatomy. A tool that allows for measurement of patient anatomy may allow for increased comfort and efficiency during patient fitting. As sizing is commonly done by hand, such a tool may also standardize communications between different clinicians for patient care or instructional purposes. The tool can include a portion for pressing against the rectovaginal septum. The tool can be configured to measure a lateral width of the vaginal cavity simultaneous to creating a protrusion of the posterior vaginal wall into the rectal space.

Figure 37:
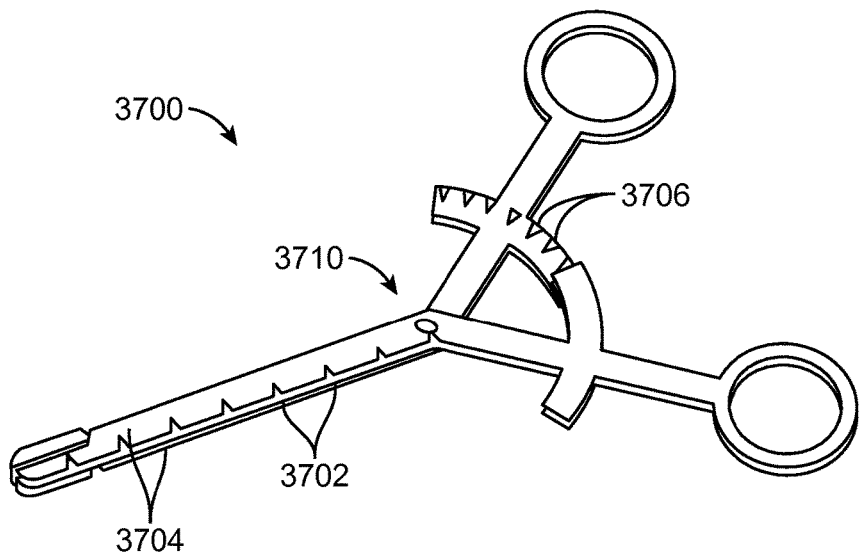
FIG. 37 illustrates an embodiment of a sizing tool.

FIG. 37 illustrates an embodiment of a tool 3700 configured to measure vaginal depth or length. Ruler-like markings 3702 on the tool surface can indicate the depth of the vagina while the tool is inserted in the vagina. Tools can also be provided to measure the width of a vaginal cavity. For example, a tool with a scissor joint 3710 mechanism can be inserted and opened within the vagina, spreading legs 3704. This mechanism can open to widths at least about 3 fold or more preferably about 5 fold, or more preferably about 10 fold greater than the insertion profile. Width markers 3706 along the external handles can indicate the width of the vagina to the clinician. In some embodiments, the legs of a measurement tool can be opened using a screw drive mechanism or hydraulic mechanism. These mechanisms may be powered manually, electrically, or pneumatically. These or other embodiments can also allow for a simple release mechanism such as a pin to quickly collapse the tool legs when measurement is complete.

In some embodiments, the physician or user may use tools within the vagina using only tactile feel to determine the desired force applied to the tissue. A tool utilizing reduced advantage on the tool handle may increase the clinician's sensitivity to pressure on the vaginal walls, thereby increasing device safety and repeatability. In other embodiments, a constant force or compression spring comprising an indication of force applied can be used to help ensure a proper amount of force is being applied. In these or other embodiments, the measuring tool can be configured to have a user interface or handle that is configured to react when the desired force is exceeded. For example the user may feel a decrease in resistance from the tool upon exceeding the desired pressure. Such a tool can use torque beams or similar mechanisms to achieve this effect. Such increased control over force applied can help improve patient comfort and safety and consistency of measurements.

FIG. 38A illustrates an embodiment of a tool 3800 comprising a shaft 3802 and a round head 3804. The tool 3800 comprises a constant force spring 3806 in the head 3804. In some embodiments, the tool comprises a ring comprising a compression spring in the head. The spring 3806 can be tensioned by an external tensile element 3808 (e.g., string, cable, cord, wire, etc.), allowing the user to change the diameter of the head 3804 by changing tension on the tensile element 3808. FIG. 38B illustrates the tool 38000 with the spring 3806 decreasing the diameter of the head 3804. The head can be configured to lay flat within the vagina in the same position as intended for the stabilizing body. The tensile element 3808 can include markings 3809 to indicate vaginal circumference. In some embodiments, the tool 3800 can be paired with an actual expandable device that can be set to the desired circumference prior to releasing the tool. In some embodiments, the tool 3800 can be removed in its higher tension state, as a small ring, or in a lower tension state, allowing it to be folded for insertion or removal.

FIG. 39A illustrates an embodiment of a tool 3900 comprising a soft body 3902 configured to increase in diameter when tensioned by the user. In this embodiment, the body or the body's shell, is at least partly incompressible, conserving volume. The tool can be inserted in its elongated, reduced-profile shape. The tool 3900 can then be expanded, by tensioning tensile element 3904 (e.g., string, wire cord, cable, etc.), under compression until tissue is contacted with the desired force. FIG. 39B illustrates the tool 3900 in an expanded configuration. Markings 3906 on the tool 3900 can indicate a circumference of the vaginal cavity. The body 3902 can comprise a cylindrical or rectangular shape. In other embodiments, the body does not need to be incompressible, but rather uses the tensile element to activate a spreading mechanism such as those described earlier.

FIG. 40A illustrates an embodiment of a tool 4000 comprising one or more force transducers mounted on a surface 4002, 4003, 4004, 4005, wherein the surface can expand diametrically upon activation of the device. The data from the force transducers 4002, 4003, 4004, 4005 can be processed to indicate a measured diameter at a measured pressure. FIG. 40B illustrates the tool 4000 as it would look expanded within an vaginal cavity. The tool 4000 can be used to indicate that the diameter at force transducers 4002, 4005 is about equal, while the diameter at force transducer 4003 is greater, and the diameter at force transducer 4004 is the greatest. Such a tool 4000 can be used to comprehensively map the vagina for proper selection of device size and shape. In other embodiments, this information can be used to generate a personalized device constructed to conform to the patient's specific anatomy.

FIG. 41A illustrates an embodiment of a tool 4100 comprising a loop 4102 extending from the tool 4100. The loop 4102 can comprise a stiff wire or polymer loop or band. The tool 4100 may resemble an endoscopic snare. The loop 4102 can be configured to expand under compression, as shown in FIG. 41B and shrink upon application of tension by the user. Markers 4104 on the handle 4106 can indicate the circumference of the loop inside the vagina.

All of the sizing tools described herein can include an extra component serving as a stand-in expandable body. Intra-vaginal devices disclosed herein may be provided with differently sized expandable bodies. As such, using an expandable body component during measuring can allow for more accurate and appropriate measurements.

FIG. 42 illustrates an embodiment of an expandable body stand-in system 4200. The system 4200 comprises an expandable body stand-in 4202 and an attached reservoir 4204 that can create a closed system for inflating the stand-in 4202. The system 4200 includes a valve 4206 to control flow. A closed system can facilitate sterilization between patients by preventing contamination to the interior of the device. FIG. 42 illustrates the system 4200 being used in conjunction with a fitting tool 4208.

FIG. 43 illustrates an embodiment of a fitting tool 4300 comprising a structure similar to the device itself. A disposable bladder 4302 of one or more sizes can be inserted into a reusable stabilizing body 4304 for fitting. The bladder can then be removed for the tool 4300 to undergo sterilization. In some embodiments, the expandable body can comprise one or more cutouts or comprise a mesh like structure to retain the bladder with easy insertion and removal, and allow for easier cleaning and autoclave sterilization between patients. In other embodiments, the bladder 4302 can be attached using male-female features, mechanical connection, magnetic connection, and the like.

An expandable body stand-in may have a fixed size. In some embodiments, the expandable body stand-in can be configured to expand to simulate the dynamic nature of the actual device, as in FIG. 42 (system 4200). An expandable stand-in can utilize a gauge or mechanism to determine the desired volume of the expandable body. In some embodiments, the expandability is accomplished by the elasticity of the stand-in, and in others by use of redundant folds or by a combination of both.

During measurement of the vaginal cavity, the opening or expansion force of the sizing tools can be calibrated such that expansion is limited by a desired amount of contact force with the body. In such embodiments, the tool can open or expand under its own internal forces (e.g., spring force). The tool can continue to expand until its expansion is balanced by forces from the vaginal walls. The balance point can help determine the optimum size of the device.

In some embodiments, the sizing tools disclosed herein can be applied to the intra-vaginal device itself, effectively making the device the sizing tool.

Personalized Devices

In some embodiments, intra-vaginal devices personalized to anatomy of a particular patient can be used. Personalized devices can increased patient comfort and accommodate a greater range of anatomies.

Figure 44A:
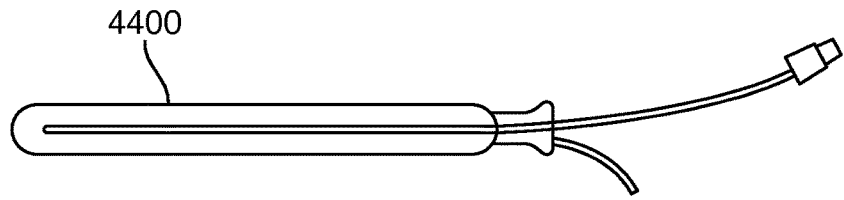
FIG. 44A-C illustrates an embodiment of a system for creating a personalized intra-vaginal device.
Figure 44B:
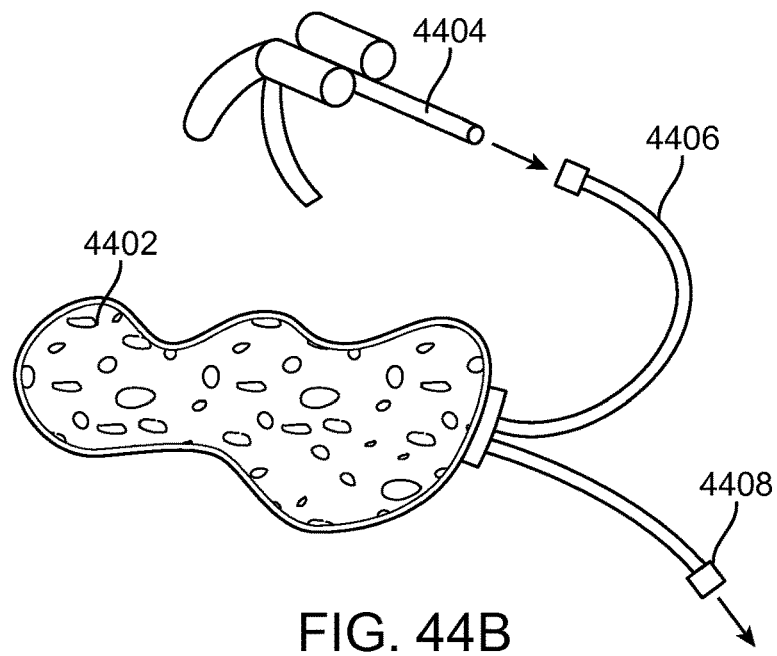
Figure 44C:
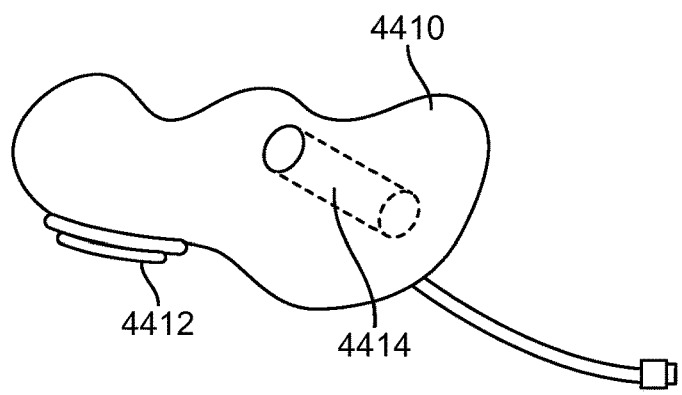

FIGS. 44A-C illustrates an embodiment of a method for creating a personalized device. As shown in FIG. 44A, a bladder 4400 can be inserted into the patient. The bladder 4400 includes an inflation lumen 4406 and a pressure relief valve 4408. After the bladder 580 is inserted into the patient, the bladder 4400 can be filled with foam 4402 (e.g., silicone, thermoplastic elastomer, or the like) using tool 4404, shown in FIG. 44B. The foam can be configured to fill the bladder and cure in place. The foam formulation can be configured to apply a desired amount of force during expansion, limited by the relief valve, or in other embodiments, by only the material composition, or in still others by the bladder elasticity or geometry without need for a valve. The cast 4410, shown in FIG. 44C can be removed and fitted with some or all of an expandable body 4412, structural elements, a drainage path 4414, insertion or removal features, or other features described herein before being reintroduced to the patient. In some embodiments, the cast 4410 can be used as an intermediate to create a more robust mold, allowing the custom shape to be made from other materials or combinations of materials. In some embodiments, the bladder may be pre-fitted with the expandable body and/or structural elements, allowing the bladder to be usable as a device with minimal effort from a clinician or user.

Another embodiment of the personalized device uses information from a sizing tool to create a device body that is specific to the patient's anatomy. This device is molded using computer aided modeling of the body, generated by inputting values, or by readings from pressure transducers like those described elsewhere in this disclosure. In another embodiment, the device is hand molded from a foam or putty that is either be cured or encased in a flexible but inelastic layer to set its final geometry. This device or one molded to match it can be tested on the patient prior to finalization. In another embodiment, material is cut or machined to shape using the same models. The materials used can be compressible, or if the part is only to be used at the stabilizing body, a more rigid material such as a polymer or rubber is used.

Toggling Check Valve

An external pump can be used to inflate the expandable body to a desired pressure. Such a pump generally comprises two check valves to control the direction of air flow and prevent backflow. The pump also generally comprises a relief valve configured to ensure that the expandable body does not exceed a predetermined pressure limit. Pump designs that reduce backflow of air during pumping can increase pumping efficiency.

Figure 45A:
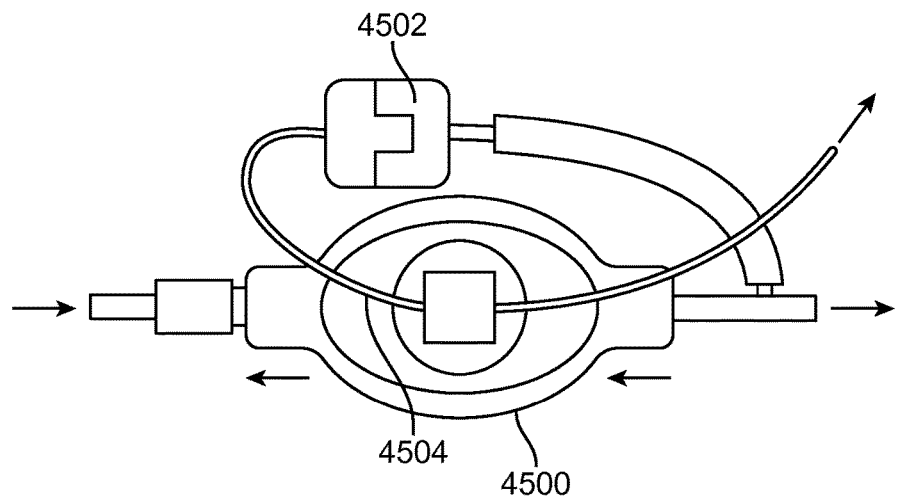
FIGS. 45A-B illustrate an embodiment of a pump.
Figure 45B:
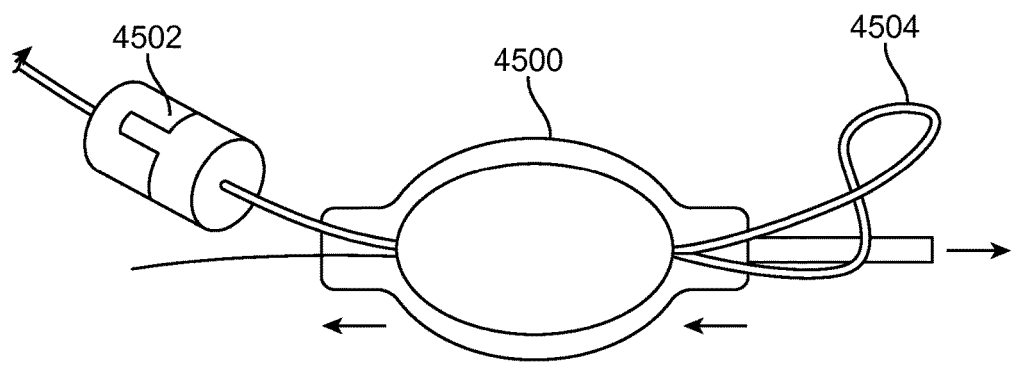

FIG. 45A illustrates an embodiment of a pump 4500 configured to cut off flow to the relief valve 4502 while the pump 4500 is being squeezed. A relief valve lumen 4504 is routed through the pump 4500, so the lumen 4504 can be compressed when the pump 4500 is squeezed. Compression of the relief valve lumen 4504 prevents air from escaping through the relief valve. FIG. 45B illustrates an alternate embodiment of pump 4500.

Alternative Pump Embodiments

Described below are several embodiments for inflating and deflating the expandable body of the device which consists of a gas or fluid reservoir. In some embodiments, the pump comprises a compressed gas cartridge with appropriate pressure limiters and relief valves. In some embodiments, the pump is electric (e.g., diaphragm pump). An electric pump can allow for various user interface control. An electric pump can also allow the clinician and/or user to set limits (e.g., pressure limits) and receive feedback regarding the state of the device or the pump.

FIG. 46 illustrates an embodiment of a pump configured to introduce a fixed volume of air or fluid, as opposed to introducing a fixed pressure. The pump 4600, shown in more detail in FIG. 46B include a syringe port 4602 configured to receive a syringe 4604. The port 4602 includes a seal 4606 configured to prevent leakage of fluid. The pump chamber 4608, configured to receive fluid, is in fluid communication with the inflation lumen 4610 (FIG. 46A).

In some embodiments, the pump comprises a hand pump with a forced completion system (e.g., a ratcheting system). Another example is a system configured to count the number of pumps and force each pump to reach completion (e.g., a linkage system).

Existing relief valves can be noisy and can often take time to reseat. In some embodiments, a pump comprises a silenced relief valve. FIG. 47A illustrates a cross sectional view of an embodiment of a spring relief valve 4700 comprising a damper 4708 contacting the poppet 4704 and the housing 4706. FIG. 47B illustrates an embodiment of an open cell or pored foam cylinder damper 4708. Incorporating the foam cylinder into the relief valve can reduce vibration noise while still allowing air through or past the foam cylinder. The foam may also assist the valve in reseating. In some embodiments, the damper shape and density can be tuned to further customize valve crack pressure.

FIGS. 48A and B illustrate an embodiment of a device 4800 and pump 4802 comprising an integrated or external interface 4804 configured to direct movement or air or fluid between two reservoirs. One reservoir 4806 is positioned in the expandable body of the device. A second reservoir 4808 is positioned in a separate location (e.g., implanted, worn externally). FIG. 48A illustrates an embodiment of a device 4800 including a second reservoir 4808 integrated with the device 4800. FIG. 48B illustrates an embodiment of a separate off-site reservoir 4808.

Figure 49A:
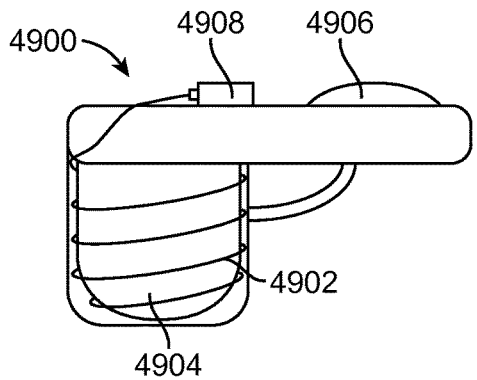
FIGS. 49A-B illustrate an embodiment of an intra-vaginal device.
Figure 49B:
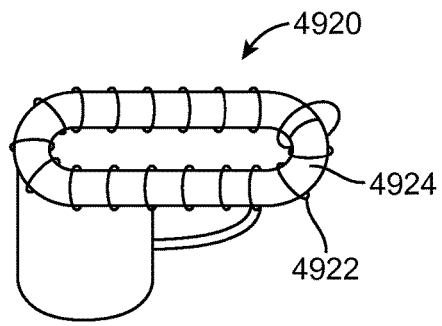

In some embodiments, fluid can be moved between reservoirs by a mechanism that causes one reservoir to contract in volume. FIG. 49A illustrates an embodiment of a device 4900 comprising a tensile element 4902 wound around the expandable body 4904. Pulling on the tensile element 4902 can cause the expandable body to contract and force fluid into the reservoir 4906. The pulling can be performed manually or by motor 4908. FIG. 49B illustrates an embodiment of a device 4920 comprising a tensile element 4922 would around a reservoir contained within the stabilizing body 4924.

Figure 50A:
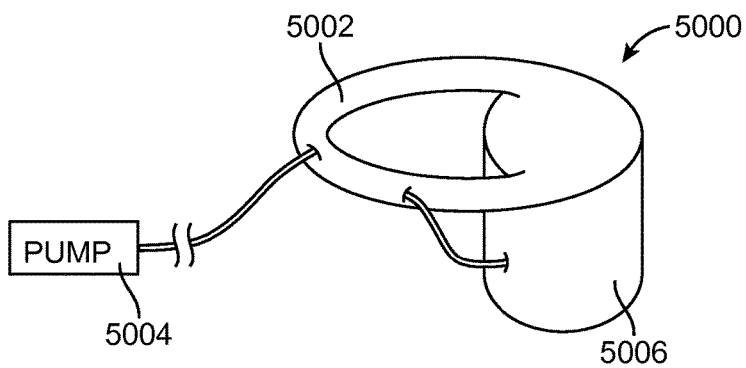
FIGS. 50A-B illustrate an embodiment of an intra-vaginal device and pump.
Figure 50B:
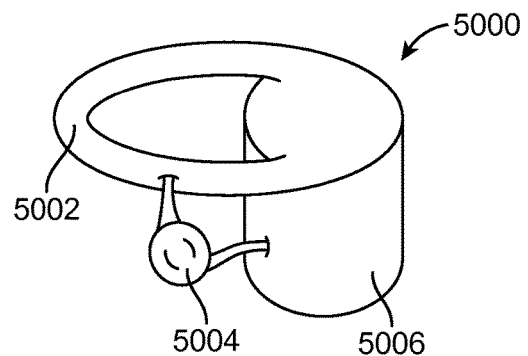

In some embodiments, a solid portion of the device, such as the stabilizing body, can act as a reservoir. The reservoir can be filled during manufacturing of the device or on an as-needed basis via a pump. FIG. 50 illustrates an embodiment of a device 5000 using valves to control flow from the stabilizing body reservoir 5002. When the pressure in the reservoir 5002 caused by pump 5004, exceeds a certain amount, the valve (not shown) can allow flow to the expandable body 5006. FIG. 50B illustrates an embodiment of the device 5000 in which the pump 5004 is in-line between the stabilizing body reservoir 5002 and the expandable body 5006.

Figure 51A:
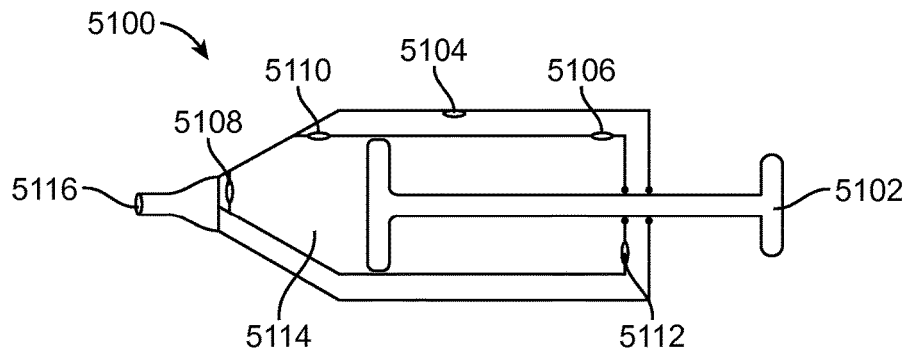
FIGS. 51A-C illustrate an embodiment of a pump.
Figure 51B:
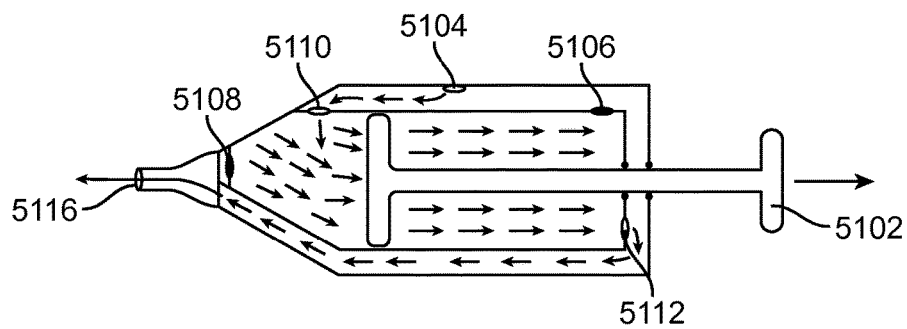
Figure 51C:
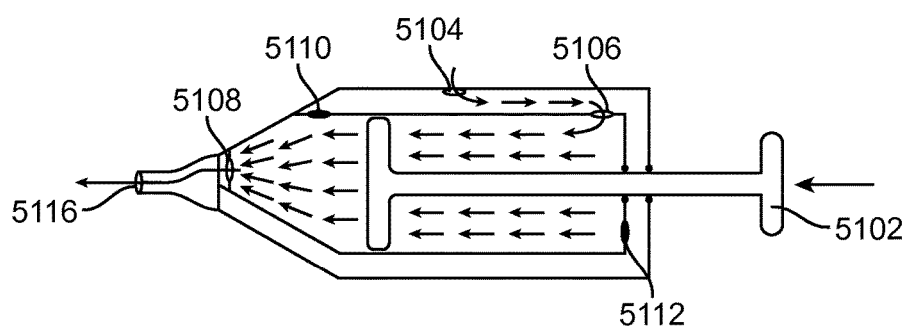

In some embodiments, the pump is configured to introduce air on both compression and retraction, increasing pump efficiency. FIG. 51 illustrates an embodiment of a dual action pump 5100. The pump 5100 comprises a piston 5102, a central inlet 5104, a chamber 5114, forward inlet 5106, forward outlet 5108, backward inlets 5110, backward outlet 5112, and a central outlet 5116. As the handle is drawn backwards, air or fluid enters central inlet and the backward inlet 5110 and fills the chamber 5114 in front of the piston 5102. Air from behind the piston 5102 flows through backward outlet 5112 and flows towards and out of the central outlet 5116. Forward inlets 5106 and forward outlet 5108 are closed as the piston moves forwards to prevent backflow. FIG. 51B illustrates the flow of air as the piston move backwards. As the piston 5102 moves forwards, as shown in FIG. 51C, air or fluid enters central inlet 5104 and forward inlet 5106 and fills chamber 5114 behind the piston 5102. The air or fluid in front of the piston 5102 is released through forward outlet 5108 and the central outlet 5116. The backward inlets 5110 are closed as the piston 5102 is moved forwards. The air built up behind the piston 5102 as the piston moves forward can then be pumped out the central outlet 5116 through backward outlet 5112 on the next pump forward.

Smart Device

In some embodiments, the intra-vaginal device has one or more incorporated smart functions. The smart functions can include one or more sensors configured to allow for capabilities such as monitoring, notification of device status, and real time stabilization. Many of the functions can be controlled using an online interface, an attachable user interface, a computer, a tablet, a smart phone, and the like. In some embodiments, some or all functions can be locked or limited by a physician.

In some embodiments, the intra-vaginal device incorporates one or more sensors. The intra-vaginal device can include a sensor configured to indicate stool buildup or passage, for example a pressure sensor on an exterior portion of the expandable body. The device can be configured to notify the user regarding stool status. In some embodiments, stool passage can trigger training signal (e.g., stimulation) to help awareness or control of stool. In some embodiments, the device can be configured to occlude the rectum only when needed such that the user is not subject to a constant force and tissues are able to be in their natural state. For example, the stool passage sensor and on board pump can be used to deflate the expandable body when occlusion is not needed.

The device can incorporate a pressure sensor in the expandable body to sense pressure within the expandable body in real time. Sensing the pressure in the expandable body can allow for control of the pressure within the expandable body. In some embodiments, the system can be integrated with an on-board pump or drive that can be used to stabilize or modify pressure. In some embodiments, the system can allow for changes in pressure of the expandable body based on changes in activity level or other physiological changes. Pressure can be adjusted to increase comfort or efficacy of the device. Changes in pressure can either be automatic, controlled by the user, or scheduled.

In some embodiments, the device incorporates sensors to monitor patient position and activity. For example, the device can incorporate position sensors, accelerometers, force transducers, or torsion transducers. Such sensors can gather information about patient position and activity for more efficacious treatment of the patient or to gather information to improve programming for the general population. Such sensors can allow the device or system to trigger specific events based on patient activity. For example, the sensor can allow the device to trigger deflation when the patient bears down to pass stool or squats in a stool passage position. For another example, the sensors can allow the patient to be warned when activity or body position may affect efficacy.

In some embodiments, the device can include powered mechanisms for collapsing or opening the device. Such mechanisms can be controlled via a user interface or application. Control can be through a wired connection, or can be performed wirelessly. Control over collapsing and opening the device can improve comfort during device insertion or removal.

In some embodiments, the device is configured to apply local stimulation or vibration to improve comfort or reduce the risk of the device applying pressure to the same location for too long a time. This may be particularly advantageous in patients with more atrophic tissue.

The device can be configured to apply a pulse to surrounding tissues or an external sphincter. The pulse can be used to trigger a bowel movement or to trigger a reflex to prevent a bowel movement. In some embodiments, the pulse is used to strengthen and tone muscles involved with bowel control, which can aid in long term ability to control bowel movements. The pulse can also be used to stimulate the sacral or other appropriate nerves to amplify internal feedback.

In some embodiments, the device can be configured to communicate with a proximity sensor. A proximity sensor can be placed in certain locations (e.g., entryway of the bathroom). The proximity sensor can interact with the device to cause predetermined actions in certain areas around the proximity sensors. For example, the device can be configured to deflate or relax to allow stool passage when the patient enters the restroom to sit.

In some embodiments, the sensors described above can be configured to track and log information relating to bowel movements and other information relevant to patient care or diagnosis. In some embodiments, the user can input other information directly and integrate it with device software. Additional metrics such as menstrual cycle information, hormone information, and the like can also be integrated for patient care of diagnosis.

Dynamically Coupled Device Component

Figure 52A:
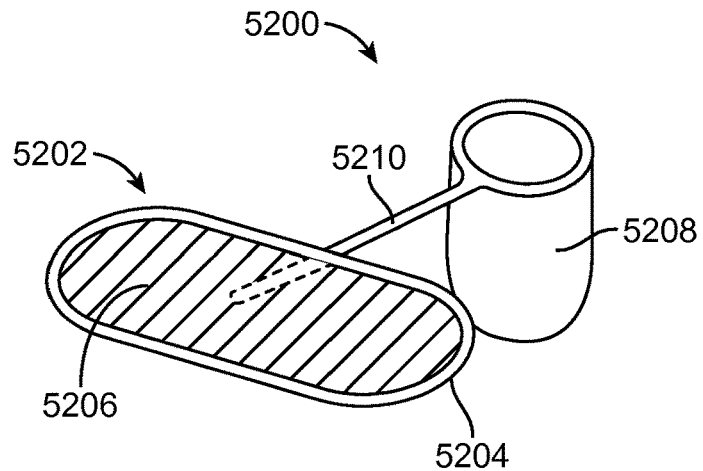
FIGS. 52A-C illustrate an embodiment of an intra-vaginal device.
Figure 52B:
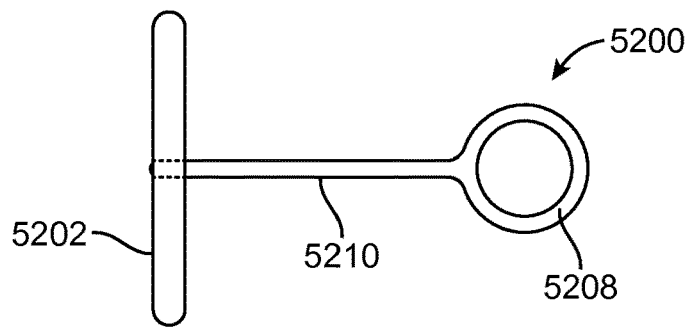
Figure 52C:
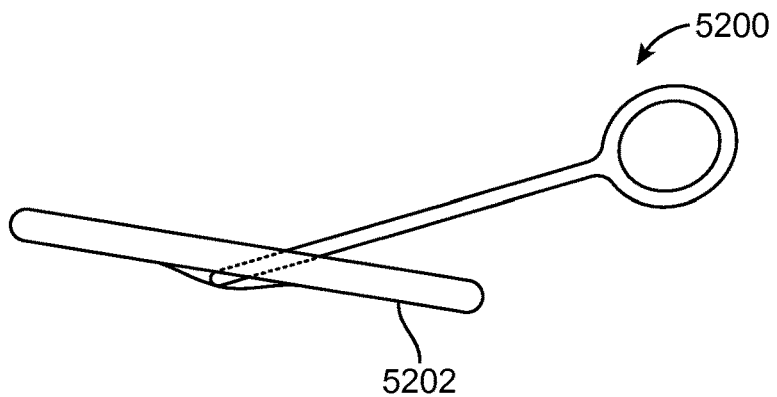

In some embodiments, the device can be stabilized by a dynamically coupled device component configured to engage distal vaginal anatomy. The dynamic stabilizing portion can be free to rotate in one or more directions, but maintains position proximal to the introitus. This dynamic capability can allow the device to adjust to differences in patient anatomies, and resist dislodgement due to relative motion in the body. FIG. 52 illustrates a perspective view of an embodiment of a device 5200 comprising a dynamic stabilizing portion 5202 comprising a frame 5204. The frame 52 is spanned by an elastomeric membrane 5206. The expandable portion 5208 is connected to the dynamic stabilizing portion 5202 by a post 5210. The post 5210 is fixed to the membrane 5206 itself. FIG. 52B illustrates a top view of the device 5200. FIG. 52C illustrates the device 5200 with the dynamic stabilizing portion 5202 deflected to one side for insertion.

Figure 53A:
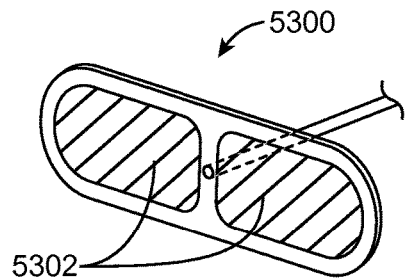
FIGS. 53A-D illustrate an embodiment of a stabilizing body of an intra-vaginal device.
Figure 53B:
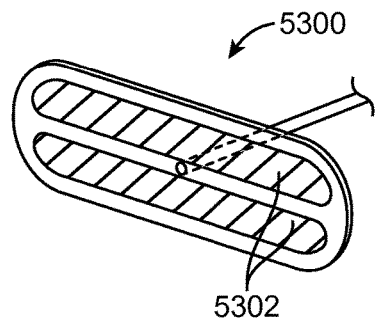
Figure 53C:
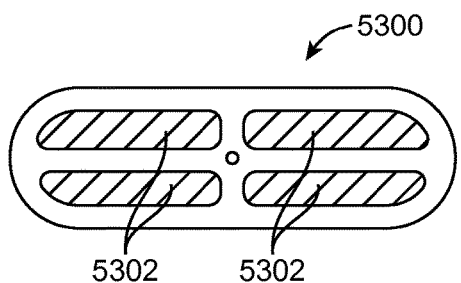
Figure 53D:
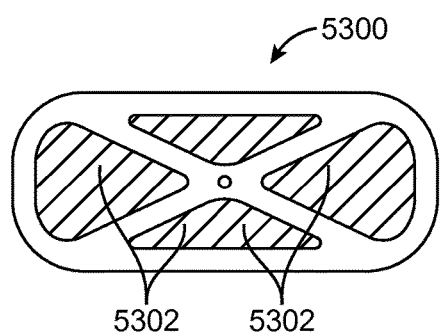

FIGS. 53A-D illustrates an embodiment of a dynamic stabilizing portion 5300 segmented into two or more sections. FIGS. 53A and B illustrate embodiments of a dynamic stabilizing portions comprising two sections 5302. The stabilizing portion 5300 of FIG. 53A is split along the length of the stabilizing portion, while the stabilizing portion 5300 is split along the width of the stabilizing portion. FIGS. 53C and D illustrate embodiments of a dynamic stabilizing portion comprising four sections 5302. The stabilizing portion 5300 of FIG. 53C comprises four segments 5302 arranged linearly in rows and columns. The stabilizing portion 5300 of FIG. 53D comprises four segments 5302 shaped generally triangularly around a center point. A segmented panel stabilizing portion can help control degrees of freedom in the motion of the panel.

Figure 54:
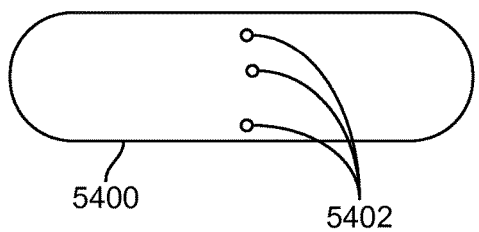
FIG. 54 illustrates an embodiment of a stabilizing body of an intra-vaginal device.

FIG. 54 illustrates various possible locations 5402 for the point of contact between the post and the stabilizing portion 5400. Varying the location of the point of contact can bias the orientation and/or mobility of the post.

Figure 55:
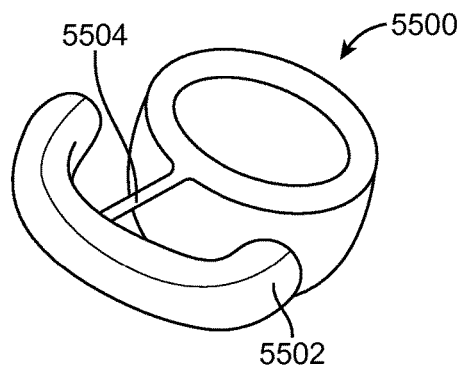
FIG. 55 illustrates an embodiment of a stabilizing body of an intra-vaginal device.

In some embodiments, the dynamic stabilizing portion comprises other shapes, for example a straight or curved bar. FIG. 55 illustrates another embodiment of a device 5500 comprising a dynamic stabilizing portion 5502. The stabilizing portion 5502 comprises a curved bar. The stabilizing portion 5502 is connected to post 5504 via a joint (not shown) that allows 103 degrees of rotational freedom about that point of contact.

In some embodiments, as described above with respect to the device incorporating smart functions, the device can be configured to apply electrical or mechanical stimulation. The location of the stimulation can be selectively distributed. For example the stimulation can be on the expandable body or portions of the stabilizing body near desired anatomical targets such as the rectovaginal septum, the deep vagina, or the vaginal opening. The spatial or temporal pattern of stimulation can be programmed by the user or clinician and controlled by an on board system or external device. The stimulation can be applied to enhance blood flow, improve sexual function, or aid in muscle training or toning. In some embodiments, the stimulation is used to treat Irritable Bowel Syndrome (IBS).

Obsolescence Features

In some embodiments, to prevent excessively long wear of the device or otherwise improve patient safety, a number of obsolescence features can be introduced. The obsolescence features can be used to create a planned device failure or to provide the patient or physician with a visual or other obvious marker that the device has reached the end of its useful life.

In some embodiments, the valve that connects the device to the inflation mechanism can be designed to wear out after a certain number of attachment or inflation cycles, preventing inflation. In some embodiments, the valve can exhibit a color change or other visual indication that replacement is needed.

In some embodiments, the device itself is made from a material that changes color after a certain amount of time of after a certain amount of time in contact with the in-situ environment (e.g., the vaginal cavity).

In some embodiments, the expandable body can be configured to wear out after a certain number of expansion cycles. In some embodiments, the expandable body can change color or provide another visual indication of the completion of a certain number of expansion cycles.

The inflation mechanism (e.g., pump) used with the device can also be configured to include obsolescence features. For example, a finite number of inflation or inflation and deflation or deflation cycles can be programmed into devices. Such programming can be accomplished using electromechanical components. In some embodiments, such programming is accomplished using mechanical components, such as a hard stop gear system or a spring component configured to fatigue and break after a certain number of cycles.

In some embodiments, collapsible device mechanisms (e.g., those described herein and in PCT Application No. PCT/US2014/016549, filed Feb. 14, 2014, and entitled "INTRA-VAGINAL DEVICES AND METHODS FOR TREATING FECAL INCONTINENCE" and U.S. application Ser. No. 14/181,576, filed on Feb. 14, 2014, entitled "INTRA-VAGINAL DEVICES AND METHODS FOR TREATING FECAL INCONTINENCE") can be made out of a material configured to wear slightly during use and eventually lose its mechanical functionality. For example, the mechanism can lose its mating surface or detent. For another example, the mechanism can comprise a latch or frame comprising a return spring configured to plastically deform over extended use. Such materials can include a hard plastic or soft, tempered metal. After losing mechanical functionality, such device will fail to lock and collapse easily, notifying the user of the need to replace the device.

Surface Construction

In some embodiments, the intra-vaginal device can comprise a surface texture configured to reduce the coefficient of friction between the device and vaginal tissue, aiding in insertion and removal. The texture can be configured to reduce friction in dry, semi-dry, or well lubricated tissue. The texture can be provided on the entire device or just certain portions of the device. In some embodiments, portions of the device (e.g., those portions grasped by the patient during insertion or removal) can be configured to allow a higher amount of friction than surrounding areas.

In some embodiments, the device comprises a coating configured to reduce or enhance friction as described above. The coating can be applied to the entire device or just portion of the device. Coatings configured to reduce friction can include a hydrophilic or amino-active coating, which can become slippery in an aqueous environment.

In some embodiments, the stabilizing body comprises material configured to provide comfortable contact with patient anatomy. For example, the stabilizing body can comprise a padding comprising a soft and thick material. For another example, the stabilizing body can comprise a padding comprising a thin material with a high durometer. The paddings can encase a fluid (e.g., air), a gel (e.g., silicone or the like), closed cell foam (e.g., silicone, polyurethane, and the like), or an open cell foam. In some embodiments, the stabilizing body comprises layers of increasing durometer. For example, the stabilizing body can comprise a high durometer polymer overmolded or sheathed with lower durometer silicone.

In some embodiments, the stabilizing body comprises large surface texture configured to improve atraumicity. For example, the stabilizing body can comprise soft bumps or ridges on the padded surfaces. For another example, the stabilizing body can comprise small concave pockets, holes, or through features that can create regional suction when tissue contacts the device surface. For yet another example, the stabilizing body can comprise large pockets, holes, or through features intended for folds of surrounding tissue to invade, increasing stability.

Figure 56A:
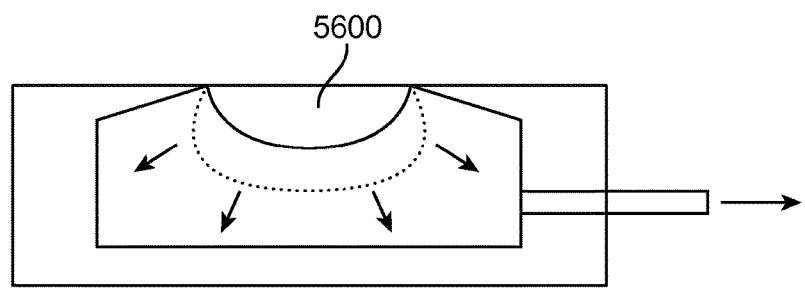
FIGS. 56A-B illustrate an embodiment of a pocket surface feature.
Figure 56B:
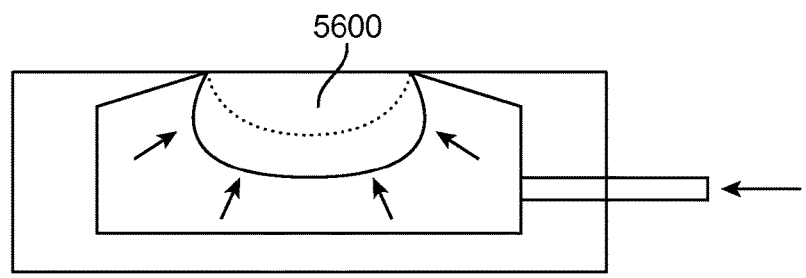

The ability of surface pockets to provide suction or allow tissue ingress can be increased by actively increasing the size of a flexible pocket. FIG. 56A illustrates an embodiment in which air is added to a pocket 5600 from one or more chambers surrounding the pocket 5600, increasing the size of the pocket 5600. Air can also be removed to decrease the size of the pocket, as shown in FIG. 56B.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" (or primary and secondary) may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An intravaginal device for the control of stool passage, the device comprising
    an expandable occluding body;
    a stabilizing body supporting the occluding body to maintain position and stability of the occluding body in the user's vagina during repeated expansions of the occluding body in an extension direction to contact the user's recto-vaginal septum to at least partially occlude the rectum, the stabilizing body comprising first and second segments that are moveable along an axis relative to one another, and the stabilizing body having first and second states, a perimeter of the device in the first state of the stabilizing body being greater than the perimeter of the device in the second state of the stabilizing body, the first and second segments defining a portion of the perimeter, the perimeter measured in a plane including the axis of the first and second segments; and
    wherein the first segment defines a recess, the second segment comprises a locking feature configured to be disposed in the recess to hold the first and second segments in a fixed position along the axis relative to one another, and the locking feature of the second segment is moveable out of the recess to allow the first and second segments to be moved along the axis relative to one another.

2. The device of claim 1, wherein a width of the stabilizing body and length of the stabilizing body can be adjusted separately between the first and second state.

3. The device of claim 1, wherein a portion of the stabilizing body to which the occluding body is attached does not change size between the first and second state.

4. The device of claim 1, wherein the first and second segments of the stabilizing body form an arm that is longer in the first state than in the second state.

5. The device of claim 4, wherein the arm is longer in the first state than in the second state due the stabilizing body being extended in the same plane as the plane that defines the perimeter.

6. The device of claim 1, wherein the stabilizing body comprises a plurality of arms.

7. The device of claim 6, wherein the stabilizing body comprises 4 arms.

8. The device of claim 6, wherein at least two of the plurality of arms are connected by a hinge.

9. The device of claim 8, wherein the hinge constrains the arms to rotational motion in the plane of the stabilizing body.

10. The device of claim 8, wherein the hinge allows angular changes between the two arms.

11. The device of claim 10, wherein the stabilizing body comprising a locking mechanism configured to maintain the two arms and the hinge in a particular angular configuration.

12. The device of claim 6, wherein all of the arms are interconnected by hinges to form a loop.

13. The device of claim 6, wherein at least one of the plurality of arms is extendible.

14. The device of claim 13, wherein all of the arms are extendible.

15. The device of claim 13, wherein the at least one extendible arm is configured to be extended by changing an amount of overlap of segments comprising the arm.

16. The device of claim 1, wherein the stabilizing body is configured to be collapsible.

17. The device of claim 1, comprising an adjustment mechanism comprising a linkage configured to expand or contract the overall perimeter of the stabilizing body.

18. The device of claim 1, wherein the first and second segments are overlapping segments configured to be pulled apart or pushed together.

19. The device of claim 1, wherein the first and second segments are configured to slide past one another.

20. The device of claim 1, wherein the stabilizing body comprises a cover.

21. The device of claim 1, wherein the occluding body is connected to the cover.

22. The device of claim 1, further comprising:
an arch member having a first end region and a second end region, the first end region being attached to one of the first and second segments of the stabilizing body; and
a ramp attached to the other of the first and second segments of the stabilizing body, the ramp and the arch member being configured such that the second end region of the arch member slides along the ramp when the first and second segments of the stabilizing body are moved axially relative to one another to provide the perimeter of the device with a rounded profile, wherein the arch forms a part of the perimeter of the device.

23. The device of claim 22, wherein one of the first and second segments is an inner segment and the other of the first and second segments is an outer segment, and the first and second segments are configured to slide relative to one another.

24. The device of claim 22, wherein a radial distance between a central region of the arch member and the one of the first and second segments to which the first end region of the arch member is attached changes as the first segment is moved axially relative to the second segment.

25. A method of selectively occluding a rectum to inhibit stool passage, comprising
inserting an intravaginal device into a user's vagina, the device comprising a stabilizing body and an occluding body, the stabilizing body comprising first and second segments that are moveable relative to one another, the first segment defining a recess, the second segment comprising a locking feature configured to be disposed in the recess to hold the first and second segments in a fixed position along an axis relative to one another, and the locking feature of the second segment being moveable out of the recess to allow the first and second segments to be moved along an axis relative to one another;
adjusting a perimeter of the stabilizing body from a first state to a second state by moving the first and second segments along an axis relative to one another, the first and second segments defining a portion of the perimeter;
engaging vaginal anatomy with the stabilizing body to stably support the occluding body; and
extending the occluding body against a recto-vaginal septum of the user to at least partially occlude the rectum.

26. The method of claim 25, wherein adjusting the perimeter of the stabilizing body comprises adjusting a distance from the occluding body to a distal portion of the device.

27. The method of claim 25, wherein adjusting the perimeter of the stabilizing body comprises adjusting the stabilizing body to position the occluding body so that it engages the recto-vaginal septum while the stabilizing body is engaging the vaginal anatomy.

28. The method of claim 25, wherein a position of the occluding body relative to a portion of the stabilizing body to which the occluding body is attached remains constant during the adjusting step.

29. The method of claim 25, wherein the device further comprises an arch member having a first end region attached to one of the first and second segments of the stabilizing body and a second end region configured to slide along a ramp attached to the other of the first and second segments of the stabilizing body, and the second end region of the arch member slides along the ramp when the first and second segments of the stabilizing body are moved axially relative to one another to provide a perimeter of the device with a rounded profile.

30. The method of claim 29, wherein one of the first and second segments is an inner segment and the other of the first and second segments is an outer segment, and adjusting the perimeter of the stabilizing body comprises sliding the first and second segments relative to one another.

31. The method of claim 29, wherein a radial distance between a central region of the arch member and the one of the first and second segments to which the first end region of the arch member is attached changes as the first segment is moved axially relative to the second segment.

* * * * *